(12) United States Patent
Ito et al.

(10) Patent No.: US 12,313,625 B2
(45) Date of Patent: May 27, 2025

(54) LIVING TISSUE MODEL DEVICE, VASCULAR WALL MODEL, VASCULAR WALL MODEL DEVICE AND METHOD OF EVALUATING TEST SUBSTANCE

(71) Applicants: FUJIFILM CORPORATION, Tokyo (JP); THE GENERAL HOSPITAL CORPORATION, Boston, MA (US)

(72) Inventors: Koju Ito, Kanagawa (JP); Chihaya Kakinuma, Kanagawa (JP); Masafumi Nishino, Kanagawa (JP); Shinji Mima, Kanagawa (JP); Craig M Neville, Boston, MA (US); Cathryn A Sundback, Boston, MA (US)

(73) Assignees: FUJIFILM CORPORATION, Tokyo (JP); THE GENERAL HOSPITAL CORPORATION

( * ) Notice: Subject to any disclaimer, the term of this patent is extended or adjusted under 35 U.S.C. 154(b) by 828 days.

(21) Appl. No.: 16/705,214

(22) Filed: Dec. 5, 2019

(65) Prior Publication Data
US 2020/0110074 A1 Apr. 9, 2020

Related U.S. Application Data

(63) Continuation of application No. PCT/US2018/036363, filed on Jun. 7, 2018, which is (Continued)

(51) Int. Cl.
*G01N 33/50* (2006.01)

(52) U.S. Cl.
CPC ..... *G01N 33/5088* (2013.01); *G01N 33/5061* (2013.01); *G01N 33/5064* (2013.01)

(58) Field of Classification Search
CPC ........... G01N 33/5088; G01N 33/5061; G01N 33/5064; G01N 15/0806; G01N 2015/086;
(Continued)

(56) References Cited

U.S. PATENT DOCUMENTS

| 5,726,060 A | 3/1998 | Bridges |
| 2004/0052768 A1 | 3/2004 | Morrison et al. |

(Continued)

FOREIGN PATENT DOCUMENTS

| CN | 1461220 A | 12/2003 |
| CN | 102124096 A | 7/2011 |

(Continued)

OTHER PUBLICATIONS

Office action dated Sep. 28, 2021 from the KIPO in a Korean patent application No. 10-2019-7036127 corresponding to the instant patent.

(Continued)

*Primary Examiner* — Jill A Warden
*Assistant Examiner* — Dwayne K Handy
(74) *Attorney, Agent, or Firm* — SOLARIS Intellectual Property Group, PLLC

(57) ABSTRACT

A living tissue model device includes: a first liquid compartment storing a liquid composition; a second liquid compartment storing a liquid composition; and a cell layered body disposed between the first liquid compartment and the second liquid compartment, as a partition between both compartments. A vascular wall model includes: a porous membrane having a honeycomb structure; a vascular endothelial cell layer disposed on one face of the porous membrane; and a smooth muscle cell layer, or a mesenchymal stem cell layer, disposed on another face of the porous membrane. A vascular wall model device includes: a first
(Continued)

liquid compartment storing a liquid composition; a second liquid compartment storing a liquid composition; and a vascular wall model disposed between the first liquid compartment and the second liquid compartment, as a partition between both compartments. Applications of these models or model devices are also provided.

23 Claims, 12 Drawing Sheets

Related U.S. Application Data a continuation of application No. 15/618,150, filed on Jun. 9, 2017, now abandoned.

(58) Field of Classification Search
CPC ...... C12M 25/04; C12N 5/069; C12N 5/0691; C12N 2502/28; C12N 2533/54
See application file for complete search history.

(56) References Cited

U.S. PATENT DOCUMENTS

| | | | |
|---|---|---|---|
| 2005/0203013 | A1 | 9/2005 | Soker et al. |
| 2007/0281353 | A1 | 12/2007 | Vacanti et al. |
| 2009/0081770 | A1 | 3/2009 | Srienc et al. |
| 2010/0135994 | A1 | 6/2010 | Banchereau et al. |
| 2010/0273200 | A1 | 10/2010 | Niwa et al. |
| 2011/0003359 | A1 | 1/2011 | Fujiyama et al. |
| 2011/0053207 | A1 | 3/2011 | Hoganson et al. |
| 2011/0091930 | A1 | 4/2011 | Vacanti et al. |
| 2011/0250585 | A1 | 10/2011 | Iigber et al. |
| 2016/0313306 | A1* | 10/2016 | Ingber .................... C12M 25/02 |
| 2017/0325933 | A1 | 11/2017 | Liu |
| 2018/0356399 | A1* | 12/2018 | Ito ...................... G01N 33/5064 |

FOREIGN PATENT DOCUMENTS

| | | | |
|---|---|---|---|
| CN | 105983134 A | 10/2016 | |
| JP | 2002-335949 A | 11/2002 | |
| JP | 2007-6987 A | 1/2007 | |
| JP | 2011-528232 A | 11/2011 | |
| JP | 5113332 B2 | 1/2013 | |
| KR | 20110044226 A | 4/2011 | |
| KR | 20200005742 A * | 1/2020 | ........... C12N 5/0691 |
| WO | 2010/008905 A2 | 1/2010 | |
| WO | 2010009307 A2 | 1/2010 | |
| WO | 2015/134918 A1 | 9/2015 | |
| WO | WO-2017040950 A1 * | 3/2017 | ........... C12Q 1/6876 |

OTHER PUBLICATIONS

Gnecco Juan S et al., "Compartmentalized Culture of Perivascular Stroma and Endothelial Cells in a Microfluidic Model of the Human Endometrium", Annals of Biomedical Engineering, Springer US, New York, vol. 45, 10.7, Jan. 20, 2017, pp. 1758-1769, XP36266967.
Extended European Search Report dated Mar. 17, 2020, issued in corresponding EP Patent Application No. 18812778.1.
English language translation of the following: Office action dated Apr. 19, 2021 from the SIPO in a Chinese patent application No. 201880037656.7 corresponding to the instant patent application. This office action translation is submitted now in order to supplement the understanding of the cited references which are being disclosed in the instant Information Disclosure Statement.
International Search Report issued in International Application No. PCT/US2018/036363 on Aug. 21, 2018.
Written Opinion of the ISA issued in International Application No. PCT/US2018/036363 on Aug. 21, 2018.
Office action dated Jun. 29, 2021 from the IPO in a Indian patent application No. 201947050700 corresponding to the instant patent application.
English Language translation of the following: Office action dated Oct. 27, 2020 from the JPO in a Japanese patent application No. 2019-565235 corresponding to the instant patent application. This office action translation is submitted now in order to supplement the understanding of the cited references which are being disclosed in the instant Information Disclosure Statement.
English language translation of the following: Office action dated Nov. 29, 2021 from the KIPO in a Korean patent application No. 10-2019-7036127 corresponding to the instant patent.
Office Action dated Mar. 18, 2021, issued by the CIPO in corresponding Canadian Patent Application No. 3,066,624.
English language translation of the following: Office action dated Feb. 24, 2021 from the JPO in a Japanese patent application No. 2019-565235 corresponding to the instant patent application.
Nishikawa et al., "Micropatterns Based on Deformation of a Viscoelastic Honeycomb Mesh", Langmuir, vol. 19, No. 15, pp. 6193-6201, Jun. 26, 2003.
Office Action dated Feb. 23, 2022, issued by the CIPO in corresponding Canadian Patent Application No. 3,066,624.
English language translation of the following: Office action dated Mar. 11, 2021, from the KIPO in a Korean patent application No. 10-2019-7036127 corresponding to the instant patent application. This office action translation is submitted now in order to supplement the understanding of the cited references which are being disclosed in the instant Information Disclosure Statement.
English language translation of the following: Office action dated Apr. 28, 2023 from the KIPO in a Korean patent application No. 10-2021-7043094 corresponding to the instant patent.
Office action dated Oct. 24, 2022 from the KIPO in a Korean patent application No. 10-2019-7036127 corresponding to the instant patent.
Office Action dated Nov. 27, 2023, issued by the EPO in corresponding EP Patent Application No. 18812778.1.

* cited by examiner (A)

(B)

Track-etched Membrane   Honeycomb Membrane

HUVEC (CD31)

HUASMC
(α-smooth muscle actin)

LIVING TISSUE MODEL DEVICE, VASCULAR WALL MODEL, VASCULAR WALL MODEL DEVICE AND METHOD OF EVALUATING TEST SUBSTANCE

CROSS-REFERENCE TO RELATED APPLICATIONS

This application is a continuation application of International Application No. PCT/US2018/036363, filed Jun. 7, 2018, the disclosure of which is incorporated herein by reference in its entirety. Further, this application claims priority from U.S. patent application Ser. No. 15/618,150, filed Jun. 9, 2017, the disclosure of which is incorporated herein by reference in its entirety.

TECHNICAL FIELD

The present disclosure relates to a living tissue model device, a vascular wall model, a vascular wall model device and a method of evaluating a test substance.

RELATED ART

Japanese Patent No. 5,113,332 discloses a blood-brain barrier in vitro model and a method of evaluating a drug using the model. The blood-brain barrier in vitro model has a structure in which a filter device referred to as a "cell culture insert" is inserted in a culture plate, and has a structure in which a brain capillary endothelial cell layer is disposed on the upper face of a filter of the cell culture insert, and in which a brain pericyte layer is disposed on the lower face of the filter of the cell culture insert, and in which an astrocyte layer is disposed at the bottom face of the culture plate.

In the blood-brain barrier in vitro model, the filter part of the cell culture insert is a laminated body of the brain capillary endothelial cell layer, a track-etched (TE) membrane and the brain pericyte layer. The laminated body is obtained by culturing brain pericytes on one face of the TE membrane, and then culturing brain capillary endothelial cells on the other face of the TE membrane.

The above blood-brain barrier in vitro model has a structure in which the space inside the culture plate is divided into two liquid compartments by the cell culture insert. Japanese Patent No. 5,113,332 discloses a method using the blood-brain barrier in vitro model, which includes adding a drug to the inner side of the cell culture insert (a liquid compartment at a side at which the brain capillary endothelial cell layer is disposed), measuring the amount of the drug that has leaked to the outer side of the cell culture insert (a liquid compartment at a side at which the brain pericyte layer is disposed), and evaluating the ability of the drug to cross the blood-brain barrier.

SUMMARY OF INVENTION

Technical Problem

In order to obtain a living tissue model device for evaluating drugs or disease states, which could replace animal testing, it is necessary to construct a cellular tissue having a structure and a function similar to those of a tissue in a living organism. From the viewpoint of constructing a cellular tissue having a structure and a function similar to those of a tissue in a living organism, it is preferable to culture cells on both faces of a porous membrane having a higher aperture than a TE membrane (TE films generally having an aperture of about 2% to about 20%), the porous membrane serving as a scaffold for cell cultivation, to obtain a cell layered body, and applying the cell layered body to a living tissue model device.

As a scaffold for cell culture, a honeycomb structure film disclosed in Japanese Patent Application Laid-open (JP-A) No. 2002-335949, and a honeycomb thin membrane disclosed in Japanese Patent Application Laid-open (JP-A) No. 2007-6987, are known. JP-A No. 2002-335949 discloses a cell layered body obtained by culturing the same type of cells (hepatocytes or cardiac myocytes) on both faces of the honeycomb structure film. JP-A No. 2007-6987 discloses a cell sheet for transplantation for skin regeneration obtained by culturing fibroblasts on one face of the honeycomb thin membrane and then culturing epithelial keratinocytes on the other face of the honeycomb thin membrane. In these two patent documents, construction of a device that can be used for, for example, drug evaluation is not achieved.

Embodiments according to the present disclosure have been devised in view of the above circumstances.

The present disclosure aims to provide a novel living tissue model device, a novel vascular wall model, a novel vascular wall model device and applications thereof, which is a problem to be solved by the present disclosure.

Solution to Problem

Specific means for solving the problem include the following aspects.

[A1] a Living Tissue Model Device Including:
- a first liquid compartment in which a liquid composition is stored;
- a second liquid compartment in which a liquid composition is stored; and
- a cell layered body disposed between the first liquid compartment and the second liquid compartment, as a partition between the first and second liquid compartments,
- the cell layered body including a porous membrane having a honeycomb structure, a cell layer containing a first type of cells and disposed on one face of the porous membrane, and a cell layer containing a second type of cells different from the first type and disposed on the other face of the porous membrane.

[A2] The living tissue model device according to [A1], wherein the first type of cells and the second type of cells are two types of cells selected from the group consisting of parenchymal cells, stromal cells, myocytes, fibroblasts, nerve cells, glial cells, endothelial cells and epithelial cells.

[A3] The living tissue model device according to [A1] or [A2], wherein the material of the porous membrane includes at least one selected from the group consisting of polybutadiene, polystyrene, polycarbonate, polysulfone, polyurethane, polylactic acid, a polylactic acid-polyglycolic acid copolymer, a polylactic acid-polycaprolactone copolymer, polyethylene terephthalate, poly(glycerol sebacate), polyacrylate, polymethacrylate, polyacrylamine, polyethylene naphthalate, polyethylene succinate, polybutylene succinate, polycaprolactone, polyamide, polyimide, a polysiloxane derivative and triacetylcellulose.

[A4] The living tissue model device according to any one of [A1] to [A3], wherein each surface of the porous membrane is covered by at least one selected from the group consisting of fibronectin, collagen, laminin, vitronectin, gelatin, perlecan, nidogen, proteoglycan, osteopontin, tenascin, nephronectin, a basement membrane matrix, a recombinant peptide and polylysine.

[A5] The living tissue model device according to any one of [A1] to [A4], wherein an average diameter of openings of through-holes in the porous membrane is from 1 µm to 20 µm, and an aperture ratio of the porous membrane is from 30% to 70%.

[A6] A method of evaluating a test substance using the living tissue model device of any one of [A1] to [A5], the method including:
  adding a test substance to at least one of the first liquid compartment or the second liquid compartment; and
  at least one of process of (i) quantifying at least one of a chemical substance contained in the first liquid compartment or a cell contained in the first liquid compartment, or (ii) quantifying at least one of a chemical substance contained in the second liquid compartment or a cell contained in the second liquid compartment.

[A7] The method of evaluating a test substance according to [A6], wherein process (i) includes quantifying at least one of a miRNA contained in the first liquid compartment, a protein contained in the first liquid compartment or a transcription factor contained in the first liquid compartment, and process (ii) includes quantifying at least one of a miRNA contained in the second liquid compartment, a protein contained in the second liquid compartment or a transcription factor contained in the second liquid compartment.

[A8] The method of evaluating a test substance according to [A6], further including adding a tracer to a liquid compartment to which the test substance has been added, wherein measuring the amount of the tracer that has leaked from the liquid compartment to which the tracer has been added to the other liquid compartment constitutes process (i) or (ii).

[B1] A vascular wall model including:
  a porous membrane having a honeycomb structure;
  a vascular endothelial cell layer disposed on one face of the porous membrane; and
  a smooth muscle cell layer disposed on the other face of the porous membrane.

[B2] The vascular wall model according to [B1], wherein a FITC-dextran 70 permeability from the vascular endothelial cell layer side to the smooth muscle cell layer side in the vascular wall model is from 0% to 10% of the FITC-dextran 70 permeability from one face of the porous membrane to the other face of the porous membrane.

[B3] A vascular wall model including:
  a porous membrane having a honeycomb structure;
  a vascular endothelial cell layer disposed on one face of the porous membrane; and
  a mesenchymal stem cell layer disposed on another face of the porous membrane.

[B4] The vascular wall model according to [B3], wherein a FITC-dextran 70 permeability from the vascular endothelial cell layer side to the mesenchymal stem cell layer side in the vascular wall model is from 0% to 10% of the FITC-dextran 70 permeability from one face of the porous membrane to the other face of the porous membrane.

[B5] The vascular wall model according to any one of [B1] to [B4], wherein the material of the porous membrane includes at least one selected from the group consisting of polybutadiene, polystyrene, polycarbonate, polysulfone, polyurethane, polylactic acid, a polylactic acid-polyglycolic acid copolymer, a polylactic acid-polycaprolactone copolymer, polyethylene terephthalate, poly(glycerol sebacate), polyacrylate, polymethacrylate, polyacrylamine, polyethylene naphthalate, polyethylene succinate, polybutylene succinate, polycaprolactone, polyamide, polyimide, a polysiloxane derivative and triacetylcellulose.

[B6] The vascular wall model according to any one of [B1] to [B5], wherein each surface of the porous membrane is covered by at least one selected from the group consisting of fibronectin, collagen, laminin, vitronectin, gelatin, perlecan, nidogen, proteoglycan, osteopontin, tenascin, nephronectin, a basement membrane matrix, a recombinant peptide and polylysine.

[B7] The vascular wall model according to any one of [B1] to [B6], wherein an average diameter of openings of through-holes in the porous membrane is from 1 µm to 20 µm, and an aperture ratio of the porous membrane is from 30% to 70%.

[C1] A vascular wall model device including a first liquid compartment in which a liquid composition is stored; a second liquid compartment in which a liquid composition is stored; and the vascular wall model of any one of [B1] to [B7] disposed between the first liquid compartment and the second liquid compartment, as a partition between the first and second liquid compartments.

[C2] A method of evaluating a test substance using the vascular wall model device of [C1], the method including:
  adding a test substance to at least one of the first liquid compartment or the second liquid compartment; and
  at least one process of (i) quantifying at least one of a chemical substance contained in the first liquid compartment or a cell contained in the first liquid compartment, or (ii) quantifying at least one of a chemical substance contained in the second liquid compartment or a cell contained in the second liquid compartment.

[C3] The method of evaluating a test substance according to [C2], wherein process (i) includes quantifying at least one of a miRNA contained in the first liquid compartment, a protein contained in the first liquid compartment or a transcription factor contained in the first liquid compartment, and process (ii) includes quantifying at least one of a miRNA contained in the second liquid compartment, a protein contained in the second liquid compartment or a transcription factor contained in the second liquid compartment.

[C4] The method of evaluating a test substance according to [C2], wherein one of the first liquid compartment or the second liquid compartment is a liquid compartment in which blood, a liquid composition containing erythrocytes or a liquid composition mimicking blood and containing at least one selected from the group consisting of dextran, Evans Blue, fluorescein sodium salt and FITC-microbeads is stored, the adding of a test substance to at least one of the first liquid compartment or the second liquid compartment includes adding the test substance to the liquid compartment in which blood, a liquid composition containing erythrocytes or a liquid composition mimicking blood and containing at least one selected from the group consisting of dextran, Evans Blue, fluorescein sodium salt and FITC-microbeads is stored, and measuring at least one of the amount of erythrocytes that have leaked from the liquid compartment to which the test substance has been added to the other liquid compartment, the amount of hemoglobin that has leaked from the liquid compartment to which the test substance has been added to the other liquid compartment or the amount of at least one selected from the group consisting of dextran, Evans Blue, fluorescein sodium salt and FITC-microbeads that has leaked from the liquid compartment to which the test substance has been added to the other liquid compartment constitutes process (i) or (ii).

[D1] A method of producing a cell layered body including a cell layer on both faces of a porous membrane, using a vessel having a bottom portion and a side wall portion standing from the periphery of the bottom portion, the porous membrane, and a holding member configured to hold the porous membrane such that the porous membrane faces the inner bottom face of the vessel and is held at a position that does not contact the inner bottom face, the method including:

culturing first cells in a liquid culture medium that contacts the inner bottom face of the vessel and a surface of the porous membrane, in a state in which the porous membrane is held, by the holding member, at a position that does not contact the inner bottom face of the vessel so as to face the inner bottom face, and in which the bottom portion of the vessel is positioned at the upper side while the porous membrane is positioned at the lower side in the direction of gravity; and culturing the first cells at the lower face of the porous membrane and culturing the second cells at the upper face of the porous membrane in a state in which the porous membrane is held, by the holding member, at a position that does not contact the inner bottom face of the vessel so as to face the inner bottom face, and in which the bottom portion of the vessel is positioned at the lower side while the porous membrane is positioned at the upper side in the direction of gravity.

Advantageous Effect

According to the present disclosure, a novel living tissue model device, a novel vascular wall model, a novel vascular wall model device and applications thereof are provided.

DESCRIPTION OF EMBODIMENTS

Embodiments of the present invention are described below. The description and the working examples provided below illustrate exemplary embodiments, and do not limit the scope of the invention. The working mechanisms described in the present disclosure include presumptions, and whether or not the presumptions are correct does not limit the scope of the invention.

In the present disclosure, each numerical range indicated using "to" refers to a range including the numbers noted before and after the "to" as the lower limit value and the upper limit value, respectively.

When two or more substances, each corresponding to a particular component in a composition, are present, the amount of the particular component in the composition described in the present disclosure means the total amount of the two or more substances present in the composition, unless otherwise specified.

<Living Tissue Model Device and Vascular Wall Model Device>

The living tissue model device according to the present disclosure includes:
a first liquid compartment in which a liquid composition is stored;
a second liquid compartment in which a liquid composition is stored; and
a cell layered body disposed between the first liquid compartment and the second liquid compartment, as a partition between the first and second liquid compartments.

The cell layered body in the living tissue model device according to the present disclosure includes:
a porous membrane having a honeycomb structure;
a cell layer containing a first type of cells and disposed on one face of the porous membrane having a honeycomb structure; and
a cell layer containing a second type of cells different from the first type and disposed on the other face of the porous membrane having a honeycomb structure.

The porous membrane having a honeycomb structure is hereinafter also referred to as a "honeycomb membrane".

In the living tissue model device according to the present disclosure, the cell layered body is disposed such that one cell layer faces the first liquid compartment and that the other cell layer faces the second liquid compartment.

In the living tissue model device according to the present disclosure, the liquid composition stored in the first liquid compartment and the liquid composition stored in the second liquid compartment may have the same composition or mutually different compositions. Each of these liquid compositions preferably has a composition configured to maintain the cells in a cell layer in the cell layered body in the living state. Examples of the liquid composition include phosphate buffer physiological saline, physiological saline, basal media for mammal cells, and blood.

Figure 1:
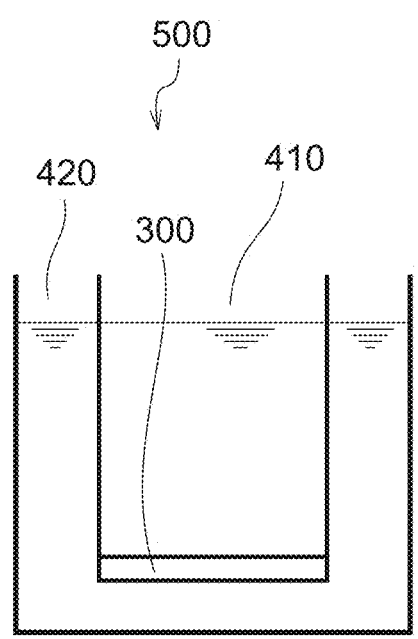
FIG. 1 is a schematic cross-sectional view illustrating one example of a living tissue model device.

A living tissue model device 500, which is one example of the living tissue model device according to the present disclosure, is illustrated in FIG. 1. FIG. 1 is a schematic cross-sectional view of the living tissue model device 500. In this figure, the size of each member is a conceptual size, and the relative relationship among the sizes of the members is not limited thereto. The living tissue model device 500 includes a first liquid compartment 410, a second liquid compartment 420 and a cell layered body 300. Each of the first liquid compartment 410 and the second liquid compartment 420 stores a liquid composition. The liquid composition stored in the first liquid compartment 410 and the liquid composition stored in the second liquid compartment 420 may have the same composition or mutually different compositions. A cell layered body 300 is a portion of a partition between the first liquid compartment 410 and the second liquid compartment 420.

An example of the configuration of the living tissue model device 500 illustrated in FIG. 1 is a configuration in which a cell culture insert is disposed in a culture vessel. The living tissue model device in this configuration includes a vessel having a bottom portion and a side wall portion standing from the periphery of the bottom portion, and a cell culture insert disposed in the vessel, and the cell culture insert includes a cell layered body. The present configuration is composed of a culture vessel and a cell culture insert obtained after a cell layered body is produced according to the below-described production method using a culture device in which the culture vessel and the cell culture insert are integrated (for example, the below-described configuration illustrated in FIG. 4B). This configuration is hereinafter referred to as a "cell culture insert-type device". When the configuration of the cell culture insert-type device is described with reference to FIG. 4B as an example, the space defined by a hollow cylindrical portion 42 of a holding member 40 and a honeycomb membrane 20 corresponds to the first liquid compartment 410 illustrated in FIG. 1, and the space defined by a bottom portion 62 of a culture vessel 60, a side wall portion 64 of the culture vessel 60, the hollow cylindrical portion 42 of the holding member 40, and the honeycomb membrane 20 corresponds to the second liquid compartment 420 illustrated in FIG. 1.

An example of the living tissue model device according to the present disclosure is a vascular wall model device. The vascular wall model device according to the present disclosure includes:
 a first liquid compartment in which a liquid composition is stored;
 a second liquid compartment in which a liquid composition is stored; and
 a vascular wall model disposed between the first liquid compartment and the second liquid compartment, as a partition between the first and second liquid compartments.

The vascular wall model in the vascular wall model device according to the present disclosure includes a honeycomb membrane, a vascular endothelial cell layer disposed on one face of the honeycomb membrane, and a smooth muscle cell layer or mesenchymal stem cell layer disposed on the other face of the honeycomb membrane. In the vascular wall model device according to the present disclosure, the vascular endothelial cell layer and the smooth muscle cell layer or mesenchymal stem cell layer in the vascular wall model are disposed such that each of the vascular endothelial cell layer and the smooth muscle cell layer/mesenchymal stem cell layer faces its corresponding liquid compartment.

In the vascular wall model device according to the present disclosure, the liquid composition stored in the first liquid compartment and the liquid composition stored in the second liquid compartment may have the same composition or mutually different compositions. The liquid compositions preferably have compositions configured to maintain vascular endothelial cells and smooth muscle cells/mesenchymal stem cells in the living state. Examples of the liquid compositions include phosphate buffer physiological saline, physiological saline, basal media for mammal cells, blood, liquid compositions containing erythrocytes, and liquid compositions mimicking blood and containing at least one selected from the group consisting of dextran, Evans Blue, fluorescein sodium salt and FITC-microbeads. In the present disclosure, the scope of blood includes blood samples such as: blood diluted with physiological saline; storable blood obtained by adding additives, such as glucose and anticoagulant agents, to blood; and fractions thereof.

An example of the configuration of the living tissue model device according to the present disclosure is a configuration in which the cell layered body 300 is a vascular wall model in the living tissue model device 500 illustrated in FIG. 1. Examples of the configuration of the living tissue model device according to the present disclosure include the above-described cell culture insert-type device.

The cell layered body in the living tissue model device according to the present disclosure, and the vascular wall model in the vascular wall model device according to the present disclosure, are described below.

[Cell Layered Body and Vascular Wall Model]

The cell layered body in the living tissue model device according to the present disclosure includes a honeycomb membrane, a cell layer containing a first type of cells and disposed on one face of the honeycomb membrane, and a cell layer containing a second type of cells different from the first type and disposed on the other face of the honeycomb membrane. The number of cell layers to be disposed on each face of the honeycomb membrane may be one, or two or more.

Figure 2:
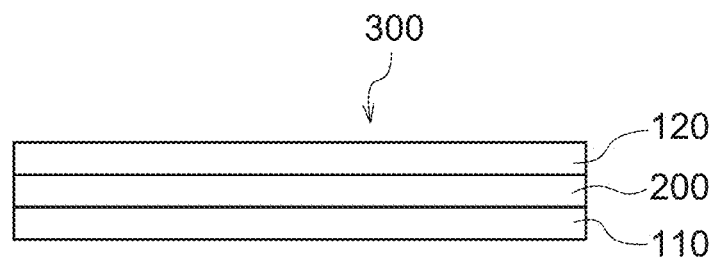
FIG. 2 is a schematic partial cross-sectional view illustrating one example of a cell layered body in a living tissue model device.

A cell layered body 300, which is one example of the cell layered body in the living tissue model device according to the present disclosure, is illustrated in FIG. 2. FIG. 2 is a schematic partial cross-sectional view of the cell layered body 300. In this figure, the size of each member is a conceptual size, and the relative relationship among the sizes of the members is not limited thereto.

The cell layered body 300 includes a honeycomb membrane 200, a cell layer 110 containing a first type of cells, and a cell layer 120 containing a second type of cells. The cell layer 110, which includes the first type of cells, is disposed on one main face of the honeycomb membrane 200, and the cell layer 120, which includes the second type of cells, is disposed on the other main face of the honeycomb membrane 200.

[Honeycomb Membrane]

The honeycomb membrane in the cell layered body according to the present disclosure serves as a scaffold to which the cells adhere and proliferate in the production of the cell layered body. More specifically, the cells proliferate on both faces of the honeycomb membrane to form a cell layer on both faces, thereby providing a cell layered body according to the present disclosure.

The honeycomb structure in the present disclosure refers to a structure in which numerous through-holes are formed by partitioning by partition walls. In the honeycomb membrane in the cell layered body according to the present disclosure, the through-holes of the honeycomb structure form openings on a main face of the honeycomb membrane. The honeycomb membrane in the cell layered body according to the present disclosure may be a membrane having a structure in which plural honeycomb structures are stacked in layers.

In the honeycomb membrane in the cell layered body according to the present disclosure, the shape of the through-holes of the honeycomb structure is not limited. The shape of the through-holes is, for example, a truncated sphere shape that lacks a part of a sphere, a barrel shape, a circular column shape, or a polygonal column shape, and through-holes in plural types of shapes may be present together. The shape of the openings of the through-holes is, for example, a circular shape, an ellipsoidal shape or a polygonal shape, and openings in plural types of shapes may be present together. In the honeycomb structure, adjacent through-holes may communicate with one another at a part.

In the honeycomb membrane, the through-holes are preferably arranged regularly from the viewpoint of increasing the homogeneity of the cell layer disposed on the honeycomb membrane. The regular arrangement may include a break or shift. However, the regular arrangement preferably includes continuous repetitions without breaks, in all directions.

One example of the honeycomb membrane is described below with reference to drawings. In each drawing, the same or equivalent element or portion is assigned the same reference character. In the description below, the longer diameter refers to the largest distance between any two points on an outline, or, in a case in which the direction is specified, refers to the longest distance between any two points in the specified direction.

Figure 3A:
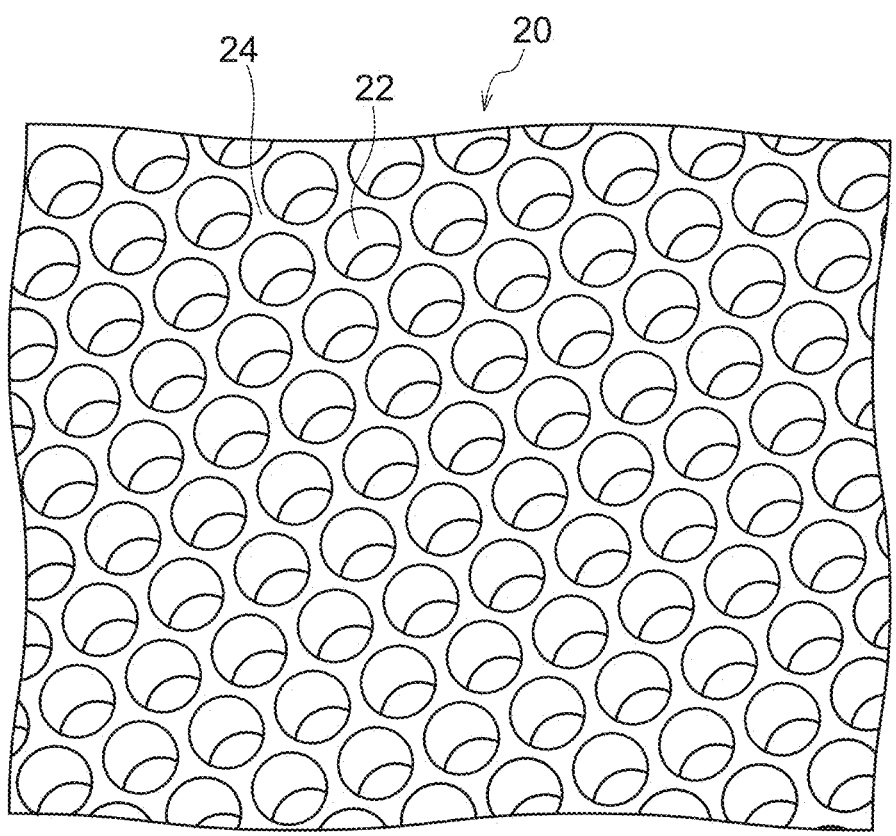
FIG. 3A is a perspective view illustrating one example of a porous membrane having a honeycomb structure.
Figure 3B:
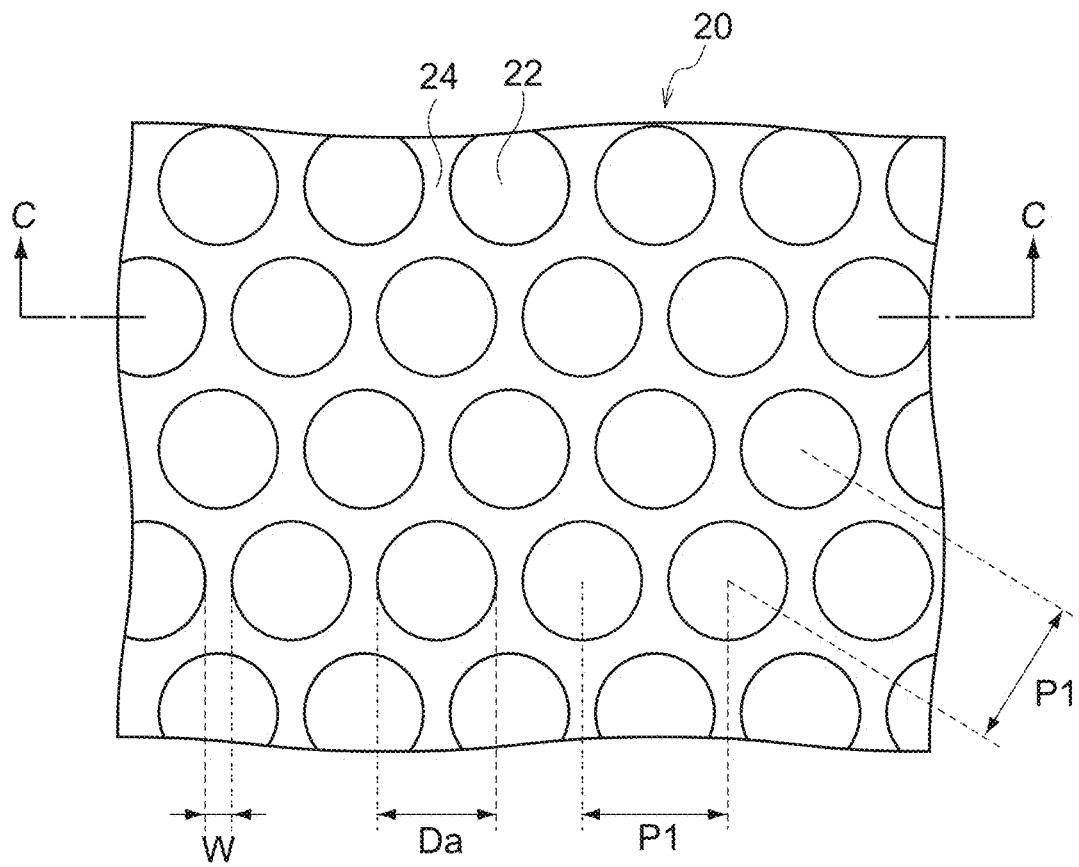
FIG. 3B is a plan view of the porous membrane illustrated in FIG. 3A viewed from the upper side.
Figure 3C:
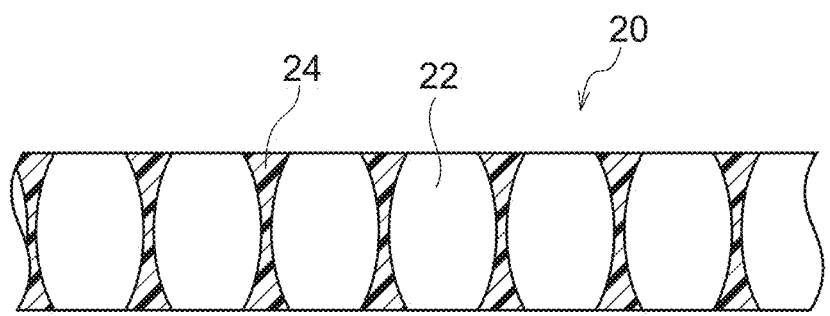
FIG. 3C is a cross-sectional view of the porous membrane taken along the line c-c in FIG. 3B.

A honeycomb membrane 20, which is one example of the honeycomb membrane, is illustrated in FIGS. 3A to 3C. FIG. 3A is a perspective view of the honeycomb membrane 20, FIG. 3B is a plan view of the honeycomb membrane 20 illustrated in FIG. 3A viewed from the upper side, and FIG. 3C is a cross-sectional view of the honeycomb membrane 20 taken along the line c-c in FIG. 3B.

Through-holes 22 are arranged over the entire area on a main face of the honeycomb membrane 20. However, when there is a region on the honeycomb membrane 20 that cannot be contacted by cells, through-holes 22 need not be provided in the region. In the honeycomb membrane 20, adjacent through-holes 22 are separated from one another by a partition wall 24.

The arrangement of the through-holes 22 is an arrangement in which a hexagon with opposite sides parallel (preferably a regular hexagon) or a similar shape serves as a unit, and in which the centers of openings are positioned at the vertices of the shape and the intersections of diagonal lines. The center of an opening refers to the center of gravity of the two-dimensional shape of the opening on a plane of the main face.

The shape of the through-holes 22 is, for example, a truncated sphere shape that lacks a part of a sphere, a barrel shape, a circular column shape, or a polygonal column shape. The shape of the openings of the through-holes 22 is, for example, a circular shape, an ellipsoidal shape or a polygonal shape. In the honeycomb structure, adjacent through-holes 22 may communicate with one another by communication holes 26, shown in FIG. 11, for example, in the interior of the honeycomb membrane 20.

The size of the honeycomb membrane 20 is described below.

The pitch P1 of the through-holes 22 is the distance between the centers of adjacent openings. The pitch P1 is preferably adjusted in accordance with the sizes of the cells contained in the cell layers disposed on the honeycomb membrane 20. The pitch P1 is, for example, from 1 μm to 50 μm.

The opening diameter Da is the longer diameter of the opening of a through-hole 22. The opening diameter Da is preferably a size that allows the cells contained in the cell layers to remain on the honeycomb membrane 20. The opening diameter Da is, for example, from 10% to 150% of the longer diameter (for example, from 10 μm to 50 μm) of the cells contained in the cell layers. When a vascular wall model is constructed in order to perform an erythrocyte leakage test, the opening diameter Da is preferably a size that allows erythrocytes to pass through. The opening diameter Da is preferably not excessively small, from the viewpoint of allowing a cell-cell contact between cells on one face and cells on the other face. On the other hand, the opening diameter Da is preferably not excessively large from the viewpoint of allowing the cells contained in the cell layers to be retained on the honeycomb membrane 20. From these viewpoints, the opening diameter Da is preferably from 1 μm to 20 μm, more preferably from 2 μm to 10 μm, and still more preferably from 3 μm to 5 μm. Similarly, the average value of the opening diameters Da of the openings is preferably from 1 μm to 20 μm, more preferably from 2 μm to 10 μm, and still more preferably from 3 μm to 5 μm.

The coefficient of variation of the opening diameter Da is preferably 20% or less, and a smaller coefficient of variation is more preferred. A smaller coefficient of variation of the opening diameter Da provides a higher homogeneity of the cell layers disposed on the honeycomb layer 20. A coefficient of variation is a value obtained by dividing a standard variation of a group by an arithmetic mean value of the group, and the coefficient of variation is an index of the degree of variations within the group. In the present disclosure, the coefficient of variation is expressed in percentage.

The width W of the partition wall 24 refers to the width of the partition wall 24 that is measured as the smallest distance between adjacent openings. The width W is preferably a width that allows the cells contained in the cell layers to be retained on the honeycomb membrane 20.

The aperture ratio of the honeycomb membrane 20 is preferably from 30% to 70%, more preferably from 35% to 65%, and still more preferably from 40% to 60%, from the viewpoints of substance permeability and the strength of the honeycomb membrane. The aperture ratio of the honeycomb membrane 20 is the ratio of the total area of the openings to the area of the main face (area including the openings) in a plan view. The aperture ratio is calculated individually for one face and the other face.

The thickness of the honeycomb membrane 20 is preferably not excessively large, from the viewpoint of allowing cell-cell contact between cells on one face and cells on the other face. The thickness of the honeycomb membrane 20 is preferably not excessively small, from the viewpoint of the strength of the honeycomb membrane 20. From these viewpoints, the thickness of the honeycomb membrane 20 is preferably from 0.5 μm to 40 μm, more preferably from 1 μm to 20 μm, and still more preferably from 2 μm to 8 μm.

The method used for producing a honeycomb membrane is not limited. Examples of methods for producing a honeycomb membrane include: production methods in which through-holes are formed by allowing water droplets to grow in a coating film containing a polymer and a solvent, which are disclosed in Japanese Patent Nos. 4,734,157, 4,945,281, 5,405,374 and 5,422,230, and Japanese Patent Application Laid-open (JP-A) No. 2011-74140; and a production method in which through-holes are formed by performing an etching treatment or punching treatment on a membrane made of a resin, to form a honeycomb membrane.

Examples of the material of the honeycomb membrane include polymers such as polybutadiene, polystyrene, polycarbonate, polyesters (for example, polylactic acid, polycaprolactone, polyglycolic acid, polylactic acid-polyglycolic acid copolymer, polylactic acid-polycaprolactone coolymer, polyethylene terephthalate, polyethylene naphthalate, polyethylene succinate, polybutylene succinate, and poly-3-hydroxybutyrate), polyacrylate, polymethacrylate, polyacrylamide, polymethacrylamide, polyvinyl chloride, polyvinylidene chloride, polyvinylidene fluoride, polyhexafluoropropene, polyvinyl ether, polyvinylcarbazole, polyvinyl acetate, polytetrafluoroethylene, polylactone, polyamide, polyimide, polyurethane, polyurea, polyaromatics, polysulfone, polyethersulfone, polysiloxane derivatives, and cellulose acylate (for example, triacethyl cellulose, cellulose acetate propionate, and cellulose acetate butyrate), poly(glycerol sebacate) and polyacrylamine. Polymers that dissolve in a hydrophobic organic solvent are preferable from the viewpoint of producing a honeycomb membrane using the production method disclosed, for example, in Japanese Patent No. 4,734,157. These polymers may have the form of a homopolymer, a copolymer, a polymer blend or a polymer alloy, as necessary, from the viewpoints of, for example, solubility in solvents, optical properties, electrical properties, membrane strength, and elasticity. These polymers may be used singly, or in combination of two or more thereof.

As the material of the honeycomb membrane, polybutadiene, polyurethane, polycarbonate or polylactic acid is preferred from the viewpoint of self-supporting properties, and polylactic acid, polylactic acid-polyglycolic acid copolymer or a polylactic acid-polycaprolactone copolymer is preferred from the viewpoint of maintaining engraftment of the cell layers.

From the viewpoint of cell adhesion property, each surface of the honeycomb membrane is preferably covered with at least one selected from the group consisting of fibronectin, collagen (for example, type I collagen, type IV collagen or type V collagen), laminin, vitronectin, gelatin, perlecan, nidogen, proteoglycan, osteopontin, tenascin, nephronectin, a basement membrane matrix, a recombinant peptide and polylysine, at least over the regions on which the cell layers are disposed. With respect to the basement membrane matrix, commercial products (for example MATRIGEL (registered trademark), GELTREX (registered trademark)) are available. With respect to the recombinant peptide, commercial products (for example, CELLNEST (registered trademark)) are available. In the honeycomb membrane, the interior of the holes are also preferably covered with at least one of these materials.

[First Type of Cells and Second Type of Cells]

In the cell layered body in the living tissue model device according to the present disclosure, the first type of cells and the second type of cells are different types of cells. The two types of cells that are the first type of cells and the second type of cells are, for example, two types of cells selected from the group consisting of parenchymal cells (for example, hepatic parenchymal cells or pancreatic parenchymal cells), stromal cells (for example, pericytes), myocytes (for example, smooth muscle cells, cardiomyocytes, or skeletal muscle cells), fibroblasts, nerve cells, glial cells, endothelial cells (for example, vascular endothelial cells or lymphatic endothelial cells), epithelial cells (for example, alveolar epithelial cells, oral epithelial cells, bile duct epithelial cells, intestinal epithelial cells, pancreatic duct epithelial cells, kidney epithelial cells, renal tubular epithelial cells or placental epithelial cells) and stem cells (for example, mesenchymal stem cells).

In the cell layered body according to the present disclosure, plural types of cells may be contained in one cell layer. In the cell layered body according to the present disclosure, one or more types of cells (referred to as a third type of cells) other than the first type of cells and the second type of cells may be contained in one of the cell layers or both of the cell layers. In an example, the first type of cells are parenchymal cells, the second type of cells are stromal cells, and the third type of cells are nerve cells, and the nerve cells may be included in one or both of the cell layers.

Even if one cell layer that contains the first type of cells also include the second type of cells, which are the same type of cells as those contained in the other cell layer, this configuration is still within the present disclosure as long as the cells contained in the one cell layer and the cells contained in the other cell layer can be differentiated based on, for example, the content ratio between the types of cells. For example, the present disclosure encompasses a configuration in which cells contained in one cell layer are parenchymal cells and stromal cells (in a content ratio of 9:1), and in which cells contained in the other cell layer are parenchymal cells and stromal cells (in a content ratio of 1:9).

The cell layered body according to the present disclosure is a tissue model mimicking a tissue in a living organism and included in the living tissue model device according to the present disclosure. Therefore, the first type of cells and the second type of cells are selected, and, if necessary, the third type of cells are selected, in accordance with the tissue in a living organism to be mimicked. In animal tissues, a basement membrane is generally present between one cell layer and another cell layer. In the cell layered body according to the present disclosure (serving as a tissue model), the honeycomb membrane corresponds to the basement membrane.

An example of a tissue model that mimics a tissue in a living organism is a vascular wall model. The vascular wall model according to the present disclosure includes a honeycomb membrane, a vascular endothelial cell layer disposed on one face of the honeycomb membrane, and a smooth muscle cell layer or mesenchymal stem cell layer disposed on the other face of the honeycomb membrane.

The vascular wall model preferably prevents chemical substances from freely passing between cells in a vascular endothelial cell layer, in other words, preferably has a barrier function. The barrier function of the vascular wall model can be expressed using a fluorescein isothiocyanate-dextran 70 (FITC-dextran 70) permeability as an index. The vascular wall model according to the present disclosure is preferably configured such that the FITC-dextran 70 permeability from the vascular endothelial cell layer side to the smooth muscle cell layer side or the mesenchymal stem cell layer side is from 0% to 10% of the FITC-dextran 70 permeability of the honeycomb membrane itself, more preferably from 0% to 5% of the FITC-dextran 70 permeability of the honeycomb membrane itself, and still more preferably from 0% to 2% of the FITC-dextran 70 permeability of the honeycomb membrane itself. In vascular wall models having such a configuration, cell-cell adhesion among vascular endothelial cells have presumably developed to a state close to vascular walls in a living organism. In order to accurately evaluate drugs using a vascular wall model, the vascular wall model desirably has a structure and a function similar to vascular walls in a living organism. Therefore, vascular wall models having the above configuration can work as an excellent means for evaluating drugs.

The method used for assaying the FITC-dextran 70 permeability in a vascular wall model will be described later.

Another example of a tissue model mimicking a tissue in a living organism is a disease state reproduction model. In this model, cells having a genetic mutation or cells from a patient are used as at least one of the first types of cells or the second types of cells.

A living tissue model device including the above-described cell layered body is useful as a device for drug evaluation or disease state evaluation, or as a device for testing capable of replacing animal testing. Next, a method of evaluating a test substance using the living tissue model device will be described as an application of the living tissue model device according to the present disclosure.

<Method of Evaluating Test Substance>

The living tissue model device according to the present disclosure may be used as a means for evaluating an effect on a cellular tissue exerted by a test substance. Specifically, the effect on a cellular tissue exerted by a test substance is evaluated using the living tissue model device according to the present disclosure, by:

adding a test substance to at least one of the first liquid compartment or the second liquid compartment; and at least one process of (i) quantifying at least one of a chemical substance contained in the first liquid compartment or a cell contained in the first liquid compartment, or (ii) quantifying at least one of a chemical substance contained in the second liquid compartment or a cell contained in the second liquid compartment.

For example, the test substance is evaluated according to the following modes (a) and (b).

(a) Mode in which a Chemical Substance Secreted from Cells of a Cell Layered Body is Quantified Cells in a cell layer located at a side facing a liquid compartment to which the test substance has been added secrete chemical substances in response to the test substance (including leakage of intracellular components due to damage to the cells). As a result, the liquid compartment to which the test substance has been added becomes to include a substance secreted from the cells. Further, cells in a cell layer at the opposite side from the cell layer facing the liquid compartment to which the test substance has been added secrete chemical substances due to at least one of a cell-cell interaction (i.e., signal transduction due to soluble factors) between the cell layer on one face and the cell layer on the other face or a cell-cell contact between the cell layer on one face and the cell layer on the other face. At least one of a substance secreted from cells contained in the liquid compartment to which the test substance has been added or a substance secreted from cells contained in the other liquid compartment is quantified, and the obtained amount is used to determine whether or not the test substance causes an effect on the cellular tissue and the degree of the effect. Examples of the substance secreted from the cells include microRNAs (miRNAs), proteins and transcription factors.

(b) Mode in which a Chemical Substance or Cells Leaking from One Side of the Cell Layered Body to the Other Side of the Cell Layered Body is Quantified Cells in a cell layer located at a side facing a liquid compartment to which the test substance has been added changes their morphology in response to the test substance (including damaging to the cells), and gaps occur in the cell layer. As a result, a chemical substance or a cell contained in the liquid composition stored in the liquid compartment to which the test substance has been added leaks out to the other liquid compartment. The chemical substance or the cell that has leaked out to the other liquid compartment is quantified, and the obtained amount is used to determine whether or not the test substance causes an effect on the cellular tissue and the degree of the effect.

One example of the mode (b) is a mode in which a tracer is used. Specifically, after a test substance is added to one liquid compartment, a tracer is added to the liquid compartment to which the test substance has been added, and the amount of the tracer that has leaked out to the other liquid compartment is quantified. In this mode, after the test substance is added to one liquid compartment, incubation is carried out, for example, at 37° C. for duration of from 30 minutes to 24 hours, and the tracer is added. In this mode, examples of the tracer include fluorescent-labeled chemical substances, chemical substances containing a radioisotope, and colorant compounds. The tracer is quantified by measuring a fluorescent intensity, a radiation or chromaticity in accordance with the type of the tracer. Whether or not the test substance causes an effect on the cellular tissue and the degree of the effect are determined based on the amount of the tracer that has leaked out to the other liquid compartment.

In the modes (a) and (b), the living tissue model device according to the present disclosure is advantageous to conventional living tissue model devices in the following respects.

Conventional living tissue model devices include a cell layered body having a cell layer on both faces of a TE membrane. TE membranes generally have an aperture ratio of as low as from about 2% to about 20%. In a cell layered body having a cell layer on both faces of a TE membrane, a cell-cell interaction between a cell layer on one face and a cell layer on the other face is relatively inactive. Therefore, there is a possibility that the cell layer at the opposite side from the cell layer located at a side facing a liquid compartment to which the test substance has been added does not perform an expected response, and does not secrete a desired chemical substance. In addition, in the cell layered body having a cell layer on both faces of a TE membrane, even if the morphology of the cells in the cell layer changes to create gaps in the cell layer, there is only a low possibility that holes in the TE membrane that have been closed by the cell layer become to penetrate through. Even if the barrier function of the cell layer is canceled by the test substance, the barrier function of the TE membrane itself may work, and may prevent the leakage of the tracer. Accordingly, conventional living tissue model devices may be incapable of accurately evaluating the effect on the cellular tissue exerted by the test substance. In particular, when the effect exerted by the test substance is weak or when the concentration of the test substance is low, it is difficult to evaluate the effect on the cellular tissue exerted by the test substance.

The living tissue model device according to the present disclosure includes a cell layered body including a cell layer on both face of a honeycomb membrane. The honeycomb membrane has a high aperture ratio. In the cell layered body including a cell layer on both faces of a honeycomb membrane, the cell-cell interaction between a cell layer on one face and a cell layer on the other face is relatively active. We presume that the active cell-cell interaction causes the cell layer at the opposite side from the cell layer located at a side facing the liquid compartment to which the test substance has been added to perform an expected response, and to secrete a desired chemical substance. Further, in the cell layered body including a cell layer on both faces of a honeycomb membrane, when the morphology of the cells in the cell layer changes to create gaps in the cell layer, the holes in the honeycomb membrane that have been closed by the cell layer become to penetrate through at high probability. Therefore, once the barrier function of the cell layer is canceled by the test substance, leakage of the tracer occurs at high probability. Accordingly, the effect on the cellular tissue exerted by the test substance can be evaluated at high sensitivity using the living tissue model device according to the present disclosure.

The vascular wall model device according to the present disclosure may be used as a means for evaluating the effect on a vascular wall exerted by a test substance. Specifically, an effect on a vascular wall exerted by a test substance is evaluated using the vascular wall model device according to the present disclosure by:

adding the test substance to at least one of the first liquid compartment or the second liquid compartment; and at least one process of (i) quantifying at least one of a chemical substance contained in the first liquid compartment or a cell contained in the first liquid compartment, or (ii) quantifying at least one of a chemical substance contained in the second liquid compartment or a cell contained in the second liquid compartment. The evaluation of the test substance is performed, for example, according to the following modes (a-1) or (b-1).

(a-1) Mode in which a Chemical Substance Secreted from Cells in the Vascular Wall Model is Quantified This mode is carried out in the same manner as that in the mode (a) described above.

(b-1) Mode in which a Chemical Substance or Cells Leaking from One Side of the Vascular Wall Model Device to the Other Side of the Vascular Wall Model Device is Quantified This mode is carried out in the same manner as that in the mode (b) described above. One example is the above-described mode in which a tracer is used. The following modes are also contemplated.

In one example of the mode (b-1), a vascular wall model device in which blood, a liquid composition containing erythrocytes or a liquid composition containing at least one selected from the group consisting of dextran, Evans Blue, fluorescein sodium salt and FITC-microbeads and mimicking blood is stored in at least one of the first liquid compartment or the second liquid compartment. In this mode, a test substance is added to a liquid compartment in which blood, a liquid composition containing erythrocytes or a liquid composition containing at least one selected from the group consisting of dextran, Evans Blue, fluorescein sodium salt and FITC-microbeads and mimicking blood is stored, and at least one of the amount of erythrocytes that have leaked to the other liquid compartment, the amount of hemoglobin that has leaked to the other liquid compartment or the amount of at least one selected from the group consisting of dextran, Evans Blue, fluorescein sodium salt and FITC-microbeads that has leaked to the other liquid compartment is quantified.

In one example of the above mode, a vascular wall model device in which blood, a liquid composition containing erythrocytes or a liquid composition containing at least one selected from the group consisting of dextran, Evans Blue, fluorescein sodium salt and FITC-microbeads and mimicking blood is stored in a liquid compartment located at a side facing a vascular endothelial cell layer is used, a test substance is added to the liquid compartment located at a side facing the vascular endothelial cell layer, and at least one of the amount of erythrocytes that have leaked to a liquid compartment located at a side facing a smooth muscle cell layer or mesenchymal stem cell layer, the amount of hemoglobin that has leaked to the liquid compartment located at the side facing a smooth muscle cell layer or mesenchymal stem cell layer or the amount of at least one selected from the group consisting of dextran, Evans Blue, fluorescein sodium salt and FITC-microbeads that has leaked to the liquid compartment located at the side facing a smooth muscle cell layer or mesenchymal stem cell layer is quantified. More specifically, the evaluation of the test substance is carried out according to the following manner.

In the vascular wall, developed cell-cell adhesion of vascular endothelial cells restricts the passage of chemical substances through the vascular wall. When the test substance has an effect on vascular endothelial cells, the vascular endothelial cells respond to the test substance (including damage to the vascular endothelial cells), and permeability of the vascular wall to chemical substances increases. As a result, erythrocytes or at least one selected from the group consisting of dextran, Evans Blue, fluorescein sodium salt and FITC-microbeads contained in the liquid composition in a liquid compartment located at a side facing the vascular endothelial cell layer leak to a liquid compartment located at a side facing the smooth muscle cell layer or mesenchymal stem cell layer. When the test substance also has a hemolytic toxicity, hemoglobin comes out of erythrocytes, and the hemoglobin leaks to the liquid compartment located at the side facing the smooth muscle cell layer or mesenchymal stem cell layer. At least one of the amount of erythrocytes that have leaked out to the liquid compartment located at the side facing the smooth muscle cell layer or mesenchymal stem cell layer, the amount of hemoglobin that has leaked out to the liquid compartment located at the side facing the smooth muscle cell layer or mesenchymal stem cell layer or the amount of at least one selected from the group consisting of dextran, Evans Blue, fluorescein sodium salt and FITC-microbeads that has leaked out to the liquid compartment located at the side facing the smooth muscle cell layer or mesenchymal stem cell layer is measured, and whether or not the test substance causes an effect on vascular walls and erythrocytes and the degree of the effect are determined based on the obtained amount.

The vascular wall model device according to the present disclosure may be used as a means for evaluating the barrier function of the vascular wall model. For example, the barrier function of the vascular wall model is evaluated, for example, using a cell culture insert-type device in which the filter portion is a vascular wall model, by assaying the FITC-dextran 70 permeability in the following manner.

A cell culture insert-type device is prepared in which the filter portion is a vascular wall model (i.e., a cell layered body in which a vascular endothelial cell layer is disposed on one face of a honeycomb membrane and in which a smooth muscle cell layer or mesenchymal stem cell layer is disposed on the other face of the honeycomb membrane), and in which the vascular endothelial cell layer faces the inner side of the cell culture insert. FITC-dextran 70 is added to the inner side of the cell culture insert and incubated at 37° C., and the amount of FITC-dextran 70 that leaks to the outer side of the cell culture insert within 10 minutes is measured (i.e., the fluorescent intensity of FITC at the outer side of the cell culture insert is measured). Separately, the amount of FITC-dextran 70 that leaks to the outer side of the cell culture insert is measured (i.e., the fluorescent intensity of FITC at the outer side of the cell culture insert is measured) using a cell culture insert-type device in which the filter portion is a honeycomb membrane itself, according to the same procedures as those described above. The ratio of the fluorescent intensity obtained in the former measurement to the fluorescent intensity obtained in the latter measurement expressed in percentage, which is the relative fluorescence intensity (RFI), is calculated. A smaller RFI value is regarded as indicating a higher barrier function of the vascular wall model. The RFI is preferably from 0% to 10%, more preferably from 0% to 5%, and still more preferably from 0% to 2%.

<Method of Producing Cell Layered Body and Living Tissue Model Device>

The living tissue model device according to the present disclosure is produced, for example, by: a method including installing a cell layered body as a partition in a living tissue model device, the cell layered body having been obtained by culturing a different type of cells on each face of a honeycomb membrane; or a method including configuring a part of a partition in a living tissue model device to be a honeycomb membrane, and culturing a different type of cells on each face of the honeycomb membrane to form a cell layered body. The method used for obtaining a cell layered body by culturing a different type of cells on each face of the honeycomb membrane may be the below-described method of producing a cell layered body. The below-described mode of the method of producing a cell layered body is also a method of producing the vascular wall model according to the present disclosure. The below-described mode of the method of producing a cell layered body is also a method of producing the cell culture insert-type device, which is one example of the living tissue model device according to the present disclosure.

In the production method according to the present disclosure, a vessel having a bottom portion and a side wall portion standing from the periphery of the bottom portion, a honeycomb membrane, and a holding member configured to hold the honeycomb membrane such that the honeycomb membrane faces the inner bottom face of the vessel and is held at a position that does not contact the inner bottom face. The vessel is hereinafter referred to as a "culture vessel".

The production method according to the present disclosure includes culturing cells on both faces of a honeycomb membrane using the culture vessel, the honeycomb membrane and the holding member, thereby producing a cell layered body having a cell layer on both faces of the honeycomb membrane.

The culture vessel, the honeycomb membrane and the holding member used in the production method according to the present disclosure will be described first. The below-described examples of the culture vessel, the honeycomb membrane and the holding member correspond to preferable examples in the cell culture insert-type device.

The culture vessel is, for example, a dish, a multi-dish or a multi-well plate. The shape of the bottom portion of the culture vessel is, for example, circular, rectangular or square. The material of the culture vessel is, for example, polystyrene, polycarbonate, polyester or glass. The culture vessel preferably has high transparency.

The inner bottom face of the culture vessel is preferably flat. The inner bottom face of the culture vessel preferably has a property such that cells do not adhere to the inner bottom face. Thus, it is preferable that the inner bottom face of the culture vessel has not been subjected to corona discharge treatment or protein coating treatment. The inner bottom face of the culture vessel may be covered with, for example, a polymer having a phosphorylcholine group or a polyethylene glycol, in order to reduce adhesion of cells. Similar to the inner bottom face, the inner side face of the culture vessel preferably has a property such that cells do not adhere to the inner side face.

The honeycomb membrane used in the production method according to the present disclosure is given the same definition as that of the honeycomb membrane included in the cell layered body, and preferable examples thereof are also the same. In the production method according to the present disclosure, the honeycomb membrane is a scaffold to which cells adhere and proliferate.

In the production method according to the present disclosure, the honeycomb membrane is a scaffold to which cells adhere and proliferate. A higher aperture ratio of the honeycomb membrane and a smaller thickness of the honeycomb membrane each provide at least one of a more active cell-cell interaction (i.e., signal transduction by soluble factors) between cells on one face and cells on the other face or a more active cell-cell contact between cells on one face and cells on the other face. A more active cell-cell interaction during cell cultivation enables production of a cell layered body having a function more close to that of a tissue in a living organism. The production method according to the present disclosure enables, for example, production of a vascular wall model in which cell-cell adhesion of vascular endothelial cells has developed to a state close to that in vascular walls in living organisms.

The holding member is a member configured to hold the honeycomb membrane such that the honeycomb membrane faces the inner bottom face of the culture vessel and is held at a position that does not contact the inner bottom face.

As the material of the holding member, resins such as polycarbonate, polystyrene and polyester are preferable in consideration of their high transparency, chemical stability in liquid culture media and light weight.

The shape of the holding member is not limited. The holding member includes, for example, a portion configured to hold the honeycomb membrane and a portion configured to contact the culture vessel. The holding member is, for example, a wire-shaped member, bar-shaped member or hollow cylindrical member that has a protruding portion engaging with the edge of the side wall portion of the culture vessel.

With respect to the morphology of the holding member, the holding member is, for example, a member including:
  a hollow cylindrical portion configured to hold a porous membrane at one axial-direction end of the hollow cylindrical portion, the cylindrical portion having a smaller outer diameter than the inner diameter of the culture vessel, and the length of the hollow cylindrical portion in the axial direction being shorter than the height of the side wall portion of the culture vessel; and
  a protruding portion protruding outwardly in the radial direction from the other axial-direction end of the hollow cylindrical portion, the protruding portion being configured to engage with the edge of the side wall portion of the culture vessel. This morphology is described below with reference to the drawings.

Figure 4A:
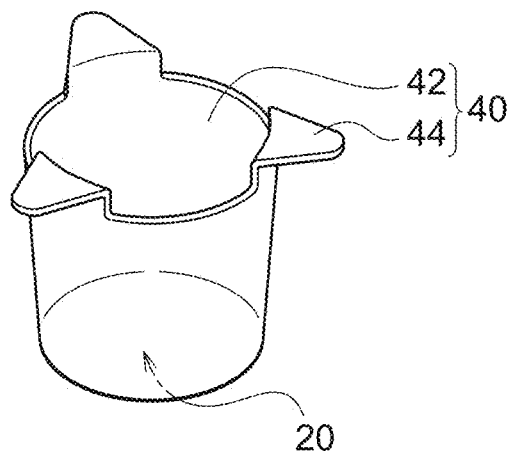
FIG. 4A is a perspective view illustrating one example of a holding member.
Figure 4B:
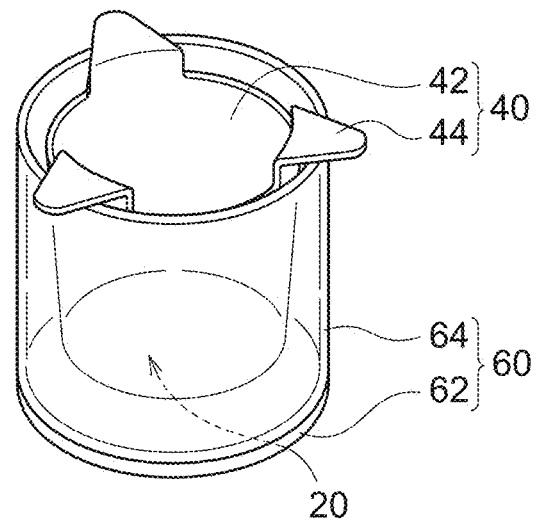
FIG. 4B is a perspective view illustrating a state in which the holding member shown in FIG. 4A is disposed in a culture vessel.

In FIG. 4A, a holding member 40, which is one example of the holding member, is illustrated in the state of being combined with the honeycomb membrane 20 (one example of the honeycomb membrane). FIG. 4A is a perspective view of the holding member 40. FIG. 4B is a perspective view illustrating a state in which the holding member 40 combined with the honeycomb membrane 20 is installed in a culture vessel 60 (one example of the culture vessel).

The holding member 40 includes a hollow cylindrical portion 42 and a protruding portion 44. The honeycomb membrane 20 is disposed at one axial-direction end of the hollow cylindrical portion 42. The honeycomb membrane 20 has a size that at least closes the opening positioned at one end of the hollow cylindrical portion 42. The honeycomb membrane 20 is adhered to one end of the hollow cylindrical portion 42 by thermal pressure bonding, ultrasonic welding, laser welding, an adhesive or a double-stick tape. Alternatively, the honeycomb membrane 20 may be fixed to one end of the hollow cylindrical portion 42 by a ring-shaped fixing member attached to the outer face of the hollow cylindrical portion 42.

The hollow cylindrical portion 42 has an outer diameter smaller than the inner diameter of the culture vessel 60, and is insertable into the inside of the culture vessel 60 (i.e., the space defined by the bottom portion 62 and the side wall portion 64). The length of the hollow cylindrical portion 42 in the axial direction is shorter than the height of the side wall portion 64 of the culture vessel 60. Therefore, the honeycomb membrane 20 does not contact the bottom portion 62 of the culture vessel 60.

The hollow cylindrical portion 42 has a wall that is continuous in the circumferential direction and the axial direction. This configuration enables a liquid to be stored in the space defined by the honeycomb membrane 20 and the hollow cylindrical portion 42. However, a slit may be provided in the wall of the hollow cylindrical portion 42 at a position near the protruding portion 44. The shape of the inner face of the hollow cylindrical portion 42 is, for example, a circular column shape, a polygonal column shape, a circular truncated cone shape or a polygonal truncated cone shape.

The protruding portion 44 protrudes outwardly in the radial direction of the hollow cylindrical portion 42 at an axial-direction end of the hollow cylindrical portion 42 opposite from an end at which the honeycomb membrane 20 is disposed. For example, three protruding portions 44 may be provided with an interval of about 120° in the circumferential direction of the hollow cylindrical portion 42. However, the number and the shape of the protruding portion 44 are not limited thereto. The protruding portion 44 may have the shape of a ring that is continuous in the circumferential direction of the hollow cylindrical portion 42.

The protruding portion 44 has a protrusion length such that the protruding portion 44 engages with the edge of the side wall portion 64 of the culture vessel 60 when the holding member 40 is inserted into the inside of the culture vessel 60. The holding member 40 is fixed at the edge of the side wall portion 64 of the culture vessel 60, due to the protruding portion 44.

The culture device having a shape as illustrated in FIG. 4A is generally called a cell culture insert.

The processes in the production method according to the present disclosure will be described next. In the present disclosure, the scope of the term "process" includes an independent process as well as a process that cannot be clearly distinguished from other processes but still achieve the desired object of the process of interest.

Figure 5:
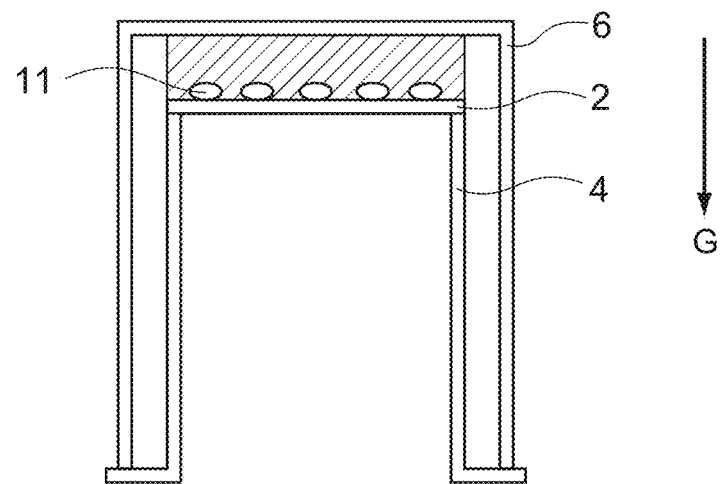
FIG. 5 is a schematic diagram illustrating one example of a method of producing a cell layered body.
Figure 5:
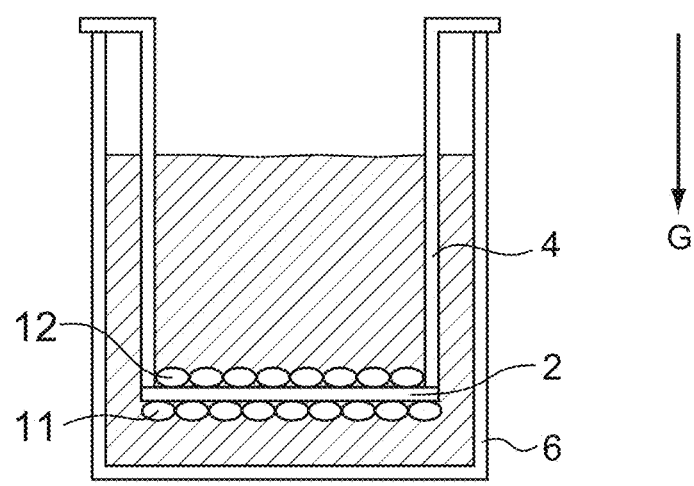

In the production method according to the present disclosure, the culture vessel, the honeycomb membrane and the holding member are used, and the production process includes the following processes (A) and (B). FIG. 5 is a schematic drawing illustrating one example of the production method according to the present disclosure, and is a schematic drawing for explaining the processes (A) and (B). In FIG. 5, the arrow G indicates the direction of gravity.

Process (A): culturing first cells 11 in a liquid culture medium that contacts the inner bottom face of the culture vessel 6 and a surface of the honeycomb membrane 2, in a state in which the honeycomb membrane 2 is held, by the holding member 4, at a position that does not contact the inner bottom face of the culture vessel 6 so as to face the inner bottom face, and in which the bottom portion of the culture vessel 6 is positioned at the upper side while the honeycomb membrane 2 is positioned at the lower side in the direction of gravity G.

Process (B): culturing the first cells 11 at the lower face of the honeycomb membrane 2 and culturing the second cells 12 at the upper face of the honeycomb membrane 2 in a state in which the honeycomb membrane 2 is held, by the holding member 4, at a position that does not contact the inner bottom face of the culture vessel 6 so as to face the inner bottom face, and in which the bottom portion of the culture vessel 6 is positioned at the lower side while the honeycomb membrane 2 is positioned at the upper side in the direction of gravity G.

The "culture" in the present disclosure does not necessarily involve proliferation of cells, and maintaining of cells in the living state is included in scope of this term regardless of the presence or absence of proliferation.

In the state adopted in the process (A), the bottom portion of the culture vessel 6 is positioned at the upper side while the honeycomb membrane 2 is positioned at the lower side in the direction of gravity G. In the process (A), a cell suspension liquid containing the first cells 11 is provided between the culture vessel 6 and the honeycomb membrane 2 such that the cell suspension liquid contacts the inner bottom face of the culture vessel 6 and a surface of the honeycomb membrane 2, and the first cells 11 are cultured in this state. Due to the surface tension acting between the inner bottom face of the culture vessel 6 and the liquid culture medium contained in the cell suspension liquid, the liquid culture medium is retained on the honeycomb membrane 2, and dropping of the liquid medium through holes in the honeycomb membrane 2 is reduced. Therefore, the honeycomb membrane having a high aperture ratio can be used for the production of the cell layered body. The honeycomb membrane 2 is preferably held, by the holding member 4, at a position near the inner bottom face of the culture vessel 6 in a state in which the honeycomb membrane 2 faces the inner bottom face of the culture vessel 6 and is oriented parallel to or substantially parallel to the inner bottom face of the culture vessel 6. The distance between the honeycomb membrane 2 and the inner bottom face of the culture vessel 6 is, for example, from 0.5 mm to 10 mm.

In the process (A), the first cells 11 in the liquid culture medium migrates in the direction of gravity G due to their own weights, and adhere to the honeycomb membrane 2. The process (A) is a process of adherent-culturing the first cells 11 on the honeycomb membrane 2.

The conditions in the cell cultivation in the process (A) may be general cell culture conditions. For example, culturing in an incubator at a temperature of 37° C. and a $CO_2$ concentration of 5% (v/v) (for example, a $CO_2$ incubator manufactured by Panasonic) may be used. The cultivation period is preferably a period until the adhesion of the first cells 11 to the honeycomb membrane 2 becomes stable.

In the state adopted in the process (B), the bottom portion of the culture vessel 6 is positioned at the lower side while the honeycomb membrane 2 is positioned at the upper side in the direction of gravity G. In the process (B), the first cells 11 are cultured at the lower face of the honeycomb membrane 2, and the second cells 12 are cultured at the upper face of the honeycomb membrane 2. The first cells 11 to be cultured at the lower face of the honeycomb membrane 2 are the first cells 11 that have been cultured on the face of the honeycomb membrane 2 located at a side facing the inner bottom face of the culture vessel 6, and the cells are continued to be cultured in the process (B).

The conditions in the cell cultivation in the process (B) may be general cell culture conditions. For example, culturing in an incubator at a temperature of 37° C. and a $CO_2$ concentration of 5% (v/v) may be used. The cultivation period is preferably a period until the cells reaches confluence on both faces of the honeycomb membrane 2. That the cells reached confluence can be detected, for example, by observation under an optical microscope. The culture medium may be changed to another culture medium during the cultivation period.

Figure 6:
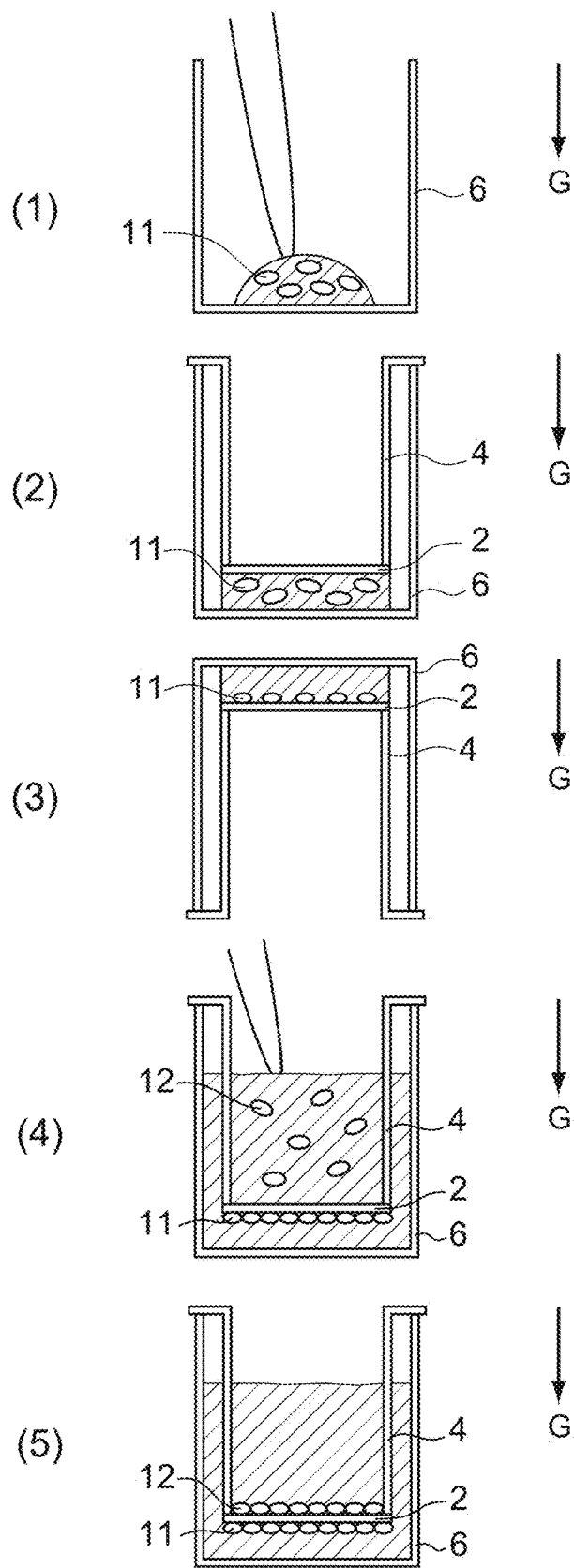
FIG. 6 is a schematic diagram illustrating one example of a method of producing a cell layered body.

One example of the production method including the process (A) and (B) will be described with reference to FIG. 6. The exemplary method illustrated in FIG. 6 is a production method using a culture device having a shape illustrated in FIG. 4B. Headings (1) to (5) in FIG. 6 correspond to the following processes (1) to (5), respectively. In FIG. 6, the arrow G indicates the direction of gravity. According to the exemplary method including the processes (1) to (5), a production method including the processes (A) and (B) can easily be realized. The exemplary method including the processes (1) to (5) is a method of producing a cell layered body, and, at the same time, a method of producing a cell culture insert-type device, which is one example of a living tissue model device.

Process (1): providing a cell suspension liquid containing the first cells 11 on the inner bottom face of the culture vessel 6.

In the process (1), it is preferable that the cell suspension liquid is provided on the inner bottom face so as not to contact the inner side face of the culture vessel 6. This is because it is desired to prevent the cell suspension liquid from falling along the inner side wall of the culture vessel 6 in the process (3). Another means for preventing the cell suspension liquid from falling along the inner side wall of the culture vessel 6 is, for example, setting the size of the honeycomb membrane 2 on its main face to a size that contacts inner side face of the culture vessel 6 over the entire circumference.

In the process (1), the amount of the cell suspension liquid provided on the inner bottom face of the culture vessel 6 is preferably an amount equivalent to the volume of the space sandwiched between the inner bottom face of the culture vessel 6 and the honeycomb membrane 2. The inoculation density of the first cells 11 is, for example, from $1.0\times10^3$ to $1.0\times10^6$ cells/cm$^2$ based on the area of the honeycomb membrane 2.

Process (2): disposing the holding member 4 equipped with the honeycomb membrane 2 in the culture vessel 6, and allowing the honeycomb membrane 2 to contact the cell suspension liquid provided on the inner bottom face of the culture vessel 6.

As a result of carrying out the process (2), the cell suspension liquid containing the first cells 11 becomes to contact the inner bottom face of the culture vessel 6 and a surface of the honeycomb membrane 2 (in other words, the cell suspension liquid becomes to be sandwiched between the inner bottom face of the culture vessel 6 and a surface of the honeycomb membrane 2). In the description of the production method below, the device in which the holding member 4 equipped with the honeycomb membrane 2 and the culture vessel 6 are integrated is referred to as a "culture device".

Process (3): culturing the first cells 11 between the inner bottom face of the culture vessel 6 and the honeycomb membrane 2, in a state in which the bottom portion of the culture vessel 6 is positioned at the upper side while the honeycomb membrane 2 is positioned at the lower side in the direction of gravity G.

The process (3) is realized by turning the culture device upside down while the holding member 4 equipped with the honeycomb membrane 2 is still attached to the culture vessel 6, and then leaving the culture device to stand still in an incubator. The first cells 11 contained in the cell suspension liquid migrate in the direction of gravity G due to their own weights and adhere to the honeycomb membrane 2.

Process (4): inoculating second cells 12 on the upper face of the honeycomb membrane 2, in a state in which the bottom portion of the culture vessel 6 is positioned at the lower side while the honeycomb membrane 2 is positioned at the upper side in the direction of gravity G.

The process (4) is realized by taking the culture device out of the incubator and turning the culture device upside down again, and then inoculating a cell suspension liquid containing the second cells 12 on the honeycomb membrane 2. The inoculation density of the second cells 12 is, for example, from $1.0\times10^3$ to $1.0\times10^6$ cells/cm$^2$. A liquid culture medium is preferably added to the first cells 11 side, before or after the second cells 12 are inoculated.

Process (5): culturing the first cells 11 on the lower face of the honeycomb membrane 2 and culturing the second cells 12 on the upper face of the honeycomb membrane 2, in a state in which the bottom portion of the culture vessel 6 is positioned at the lower side and the honeycomb membrane 2 is positioned at the upper side in the direction of gravity G.

The process (5) is realized by, subsequent to the process (4), leaving the culture device to stand still in an incubator. The culture medium may be changed to another culture medium during the period of the process (5). When at least one of the first cells 11 or the second cells 12 are stem cells, a differentiation-inducing factor that induces differentiation into desired somatic cells is added to the culture medium.

Through the processes (1) to (5), a cell layered body including the honeycomb membrane 2, a cell layer containing the first cells 11 and disposed on one face of the honeycomb membrane 2, and a cell layer containing the second cells 12 and disposed on the other face of the honeycomb membrane 2 is obtained.

The cells for use in the production method according to the present disclosure is described below.

In the production method according to the present disclosure, the first cells and the second cells are different types of cells, and the combination of the cell types is selected in accordance with the living tissue to be mimicked by the cell layered body according to the present disclosure. The two types of cells of the first cells and the second cells are, for example, two types of cells selected from the group consisting of parenchymal cells (for example, hepatic parenchymal cells or pancreatic parenchymal cells), stromal cells (for example, pericytes), myocytes (for example, smooth muscle cells, cardiomyocytes, or skeletal muscle cells), fibroblasts, nerve cells, glial cells, endothelial cells (for example, vascular endothelial cells or lymphatic endothelial cells) and epithelial cells (for example, alveolar epithelial cells, oral epithelial cells, bile duct epithelial cells, intestinal epithelial cells, pancreatic duct epithelial cells, kidney epithelial cells, renal tubular epithelial cells or placental epithelial cells), and cells capable of differentiating into any of these (for example, progenitor cells, mesenchymal stem cells or pluripotent stem cells).

Examples of pluripotent stem cells that may be used as the first cells or the second cells include embryonic stem (ES)

cells, induced pluripotent stem (iPS) cells, embryonic germ (EG) cells, embryonic carcinoma (EC) cells, multipotent adult progenitor (MAP) cells, adult pluripotent stem (APS) cells, and multi-lineage differentiating stress enduring (Muse) cells. In the process (B) of the production method according to the present disclosure, a differentiation-inducing factor that induces differentiation into the desired somatic cells is added to the culture medium, thereby differentiating the pluripotent stem cells into the somatic cells.

In the production method according to the present disclosure, a different type of cells (also referred to as the "third cells", which may be of one type or plural types) from the first cells and the second cells may be co-cultured with at least one of the first cells or the second cells. As a result of the co-culturing, a cell layer containing the third cells as well as the first or second cells is formed on one face or both faces of the honeycomb membrane. In an exemplary combination, the first cells are parenchymal cells, the second cells are stromal cells, and the third cells are nerve cells.

In the production method according to the present disclosure, the combination of the first cells and the second cells may be selected, and, if necessary, the third cells are selected, in accordance with the tissue in a living organism to be mimicked, whereby a tissue model mimicking the tissue in a living organism is obtained. In one example of the production method according to the present disclosure, the first cells are smooth muscle cells or cells differentiating into smooth muscle cells, and the second cells are vascular endothelial cells or cells differentiating into vascular endothelial cells. In another example of the production method according to the present disclosure, the first cells are mesenchymal stem cells, and the second cells are vascular endothelial cells or cells differentiating into vascular endothelial cells. The production method according to the present disclosure provides a cell layered body in which a vascular endothelial cell layer is disposed on one face of a honeycomb membrane, and a smooth muscle cell layer or a mesenchymal stem cell layer is disposed on the other face of the honeycomb membrane, i.e., provides a vascular wall model.

Cells having a genetic mutation or cells from a patient may be used as at least one of the first cells or the second cells, with a view to reproducing a disease state.

The liquid culture medium to be used for the preparation of a cell suspension liquid or cell culture is selected in accordance with the type of the cells of interest. Examples of specific culture media include culture media optimized for the cell type by adding cell growth factors to a basal medium for mammalian cells such as Dulbecco's modified Eagle's medium (DMEM), Dulbecco's modified Eagle medium: nutrient mixture F-12 (DMEM: F-12), Eagle's minimal essential medium (EMEM), minimum essential medium alpha (MEMα), or basal medium Eagle (BME). These culture media are commercially available. The liquid culture medium may be a culture medium obtained by mixing two or more culture media, in accordance with the types of cells to be co-cultured. The pH of the liquid culture medium is, for example, from 7.0 to 8.0. The liquid culture medium preferably has a specific gravity and a viscosity that allow cells to migrate in the direction of gravity due to their own weights.

EXAMPLES

Embodiments of the present disclosure are described below with reference to examples. However, embodiments of the present disclosure are not limited by these examples.

In the following description, "M" used in relation to the concentrations of a substance refers to a molar concentration, and 1 M corresponds to 1 mol/L.

The identity of the chemical substances and the like used in the examples below and indicated by their abbreviations is as follows.

EGM: endothelial cell growth medium
FITC: fluorescein isothiocyanate
HBSS: Hanks' balanced salt solution
HCM: honeycomb membrane
HUASMC: human umbilical artery smooth muscle cell
HUVEC: human umbilical vein endothelial cell
PBS: phosphate buffered saline
TEM: track-etched membrane

Example 1

Figure 7:
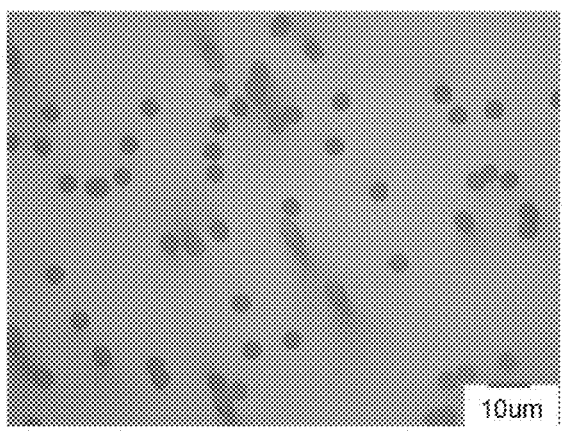
FIG. 7 is a micrograph of a porous membrane used in Examples.
Figure 7:
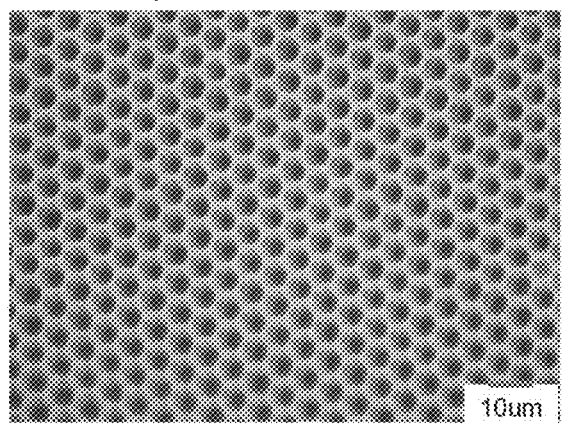

[Material]
  24-well plate: suspension culture quality (#662-102, Greiner)
  TEM insert: 24-well hanging insert, track-etched membrane (having a pore size of 5.7 μm, a thickness of 10.6 μm, and an aperture ratio of 12.4%, polyethylene terephthalate, FIG. 7) (#MCMP24H48, Millipore)
  HCM insert: 24-well hanging insert, honeycomb membrane (having a pore size of 5.0 μm, a thickness of 2.2 μm, and an aperture ratio of 55%, polybutadiene, FIG. 7)
  coating protein: fibronectin (#33016-015, Invitrogen)
[Cells]
  vascular endothelial cell: HUVEC (#C2517AS, Lonza)
  smooth muscle cell: HUASMC (#C-12500, PromoCell)
[Cell Culture Medium and Detachment Reagent]
  EGM-2 (#CC-3162, Lonza) for HUVEC.
  Smooth Muscle Cell Growth Medium 2 Kit (#C-22162, PromoCell) for HUASMC
  Accutase (AT104-500, Innovative cell technologies)
[Sterilization of HCM]
  (1) 70% (v/v) ethanol was added, in an amount of 500 μl/well, into wells of one 24-well plate, and PBS was added, in an amount of 500 μl/well, into wells of two other 24-well plates. Separately, a cup to which 70% (v/v) has been added was prepared.
  (2) HCM inserts were immersed in the ethanol in the cup, and then the HCM inserts were placed in wells containing ethanol such that their HCMs were immersed in ethanol, and the HCM inserts were left to stand still for 5 minutes.
  (3) The HCM inserts were taken out of the ethanol, and ethanol was removed from the inner side of each HCM insert using an aspirator. The HCM inserts were immediately transferred into wells containing PBS and placed such that their HCMs were immersed in PBS. 1 ml of PBS was added thereto.
  (4) The HCM inserts were taken out of the PBS, and PBS was removed from the inner side of each HCM insert using an aspirator. The HCM inserts were immediately transferred into wells containing PBS, and placed such that their HCMs were immersed in PBS. 1 ml of PBS was added thereto.
  (5) The HCM inserts being immersed in PBS were put in a vacuum desiccator, thereby deaerating the HCMs.
  (6) The HCM inserts were observed under a microscope to confirm that the HCM inserts were free of breakage, attaching matters and HCM wrinkles.

[Fibronectin Coating of HCM]
(1) Fibronectin was dissolved in PBS, to prepare a 30 µg/ml fibronectin solution.
(2) 70 µl of the fibronection solution was spotted on central portions of wells of a 24 well-plate.
(3) The HCM inserts were taken out of the PBS, and PBS was removed from the inner side of each HCM insert using an aspirator and the HCM inserts were immediately put on the fibronectin solution spots on the wells, to immerse their HCMs in the fibronectin solution.
(4) 100 µl of the fibronectin solution was added to the inner side of each HCM insert, and was left to stand still at room temperature for one hour (or left to stand still at 4° C. overnight).

[Cell Culture Using HCM Insert]
(1) 80 µl of a cell suspension liquid of HUASMCs was put, in a dome shape, on central portions of wells of a 24-well plate.
(2) The coated HCM inserts were each placed on the cell suspension liquid of HUASMCs, thereby sandwiching the cell suspension liquid between the bottom face of the well and the HCM.
(3) The plate and the HCM inserts were turned upside down in a state in which the cell suspension liquid was sandwiched between the bottom face of the well and the HCM. The plate and the HCM inserts in the turned state were placed in an incubator (37° C., 5% (v/v) $CO_2$) and culturing was performed for 16 hours.
(4) 1200 µl of a smooth muscle cell growth medium 2 kit was added to the outer side of each HCM insert. The plate and the HCM inserts were taken out of the incubator, and the orientation of the plate and the HCM inserts was returned to the initial orientation, and the HCM inserts were transferred to wells that contained a culture medium. Thereafter, 300 µl of a cell suspension liquid of HUVECs was inoculated in the inner side of each HCM insert.
(5) The plate and the HCM inserts were put in an incubator (37° C., 5% (v/v) $CO_2$), and cultured for 80 hours.

The inoculation conditions for the respective types of cells were as follows.

HUASMC: the culture area was 0.785 $cm^2$, the inoculation density was $1.0 \times 10^4$ cells/$cm^2$, and the volume of the cell suspension liquid was 80 µl.

HUVEC: the culture area was 0.32 $cm^2$, the inoculation density was $5.0 \times 10^4$ cells/$cm^2$, and the volume of the cell suspension liquid was 300 µl.

Figure 8:
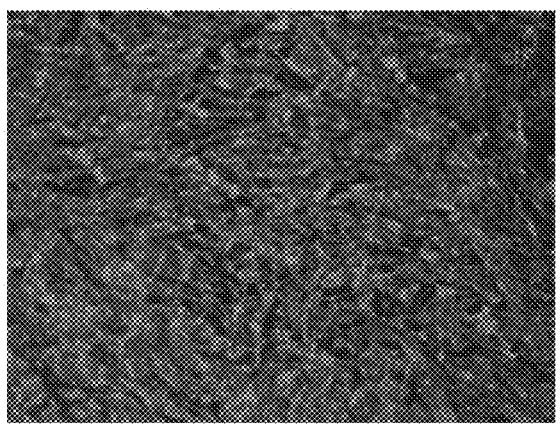
FIG. 8 is an immunofluorescent image of each cell layer formed on either face of the porous membrane.
Figure 8:
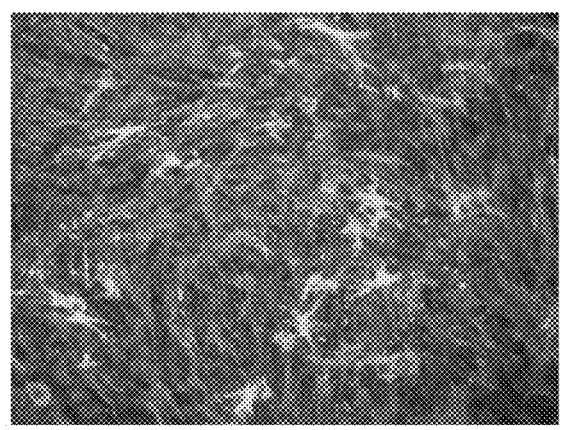

As a result of the above cultivation, HCM inserts in which a vascular endothelial cell layer was provided on the upper face of the filter, and in which a smooth muscle cell layer was provided on the lower face of the filter (also referred to as the "VEC/SMC-HCM inserts") were obtained. The cell layer on the upper face immunofluorescence-stained for CD31, and the cell layer on the lower face immunofluorescence-stained for α-smooth muscle actin, are shown in FIG. 8.

In a manner similar to the above procedures, HCM inserts in which a vascular endothelial cell layer was provided on the upper face of the filter and in which no cell layer was provided on the lower face of the filter (also referred to as the "VEC-HCM insert"), and HCM inserts in which a smooth muscle cell layer was provided on the lower face of the filter and in which no cell layer was provided on the upper face of the filter (also referred to as the "SMC-HCM insert"), were prepared.

[Cell Culture Using TEM Insert]
In a state in which the TEM inserts were placed upside down, HUASMCs were inoculated on their filters, the TEM inserts were put in an incubator (37° C., 5% (v/v) $CO_2$), and culturing was performed for 16 hours. Then, the TEM inserts were placed in wells of a 24-well plate, HUVECs were inoculated in the inner side of each TEM insert, and 1200 µl of a smooth muscle cell growth medium 2 kit was added to the outer side of each TEM insert. Then, the TEM inserts were put in an incubator (37° C., 5% (v/v) $CO_2$) and culturing was performed for 80 hours.

The conditions for inoculating cells into the TEM inserts were the same as the inoculation conditions for the cells into the HCM inserts.

As a result of the above cultivation, TEM inserts in which a vascular endothelial cell layer was provided on the upper face of the filter and in which a smooth muscle cell layer was provided on the lower face of the filter (also referred to as the "VEC/SMC-TEM insert") were obtained.

In a manner similar to the above procedures, TEM inserts in which a vascular endothelial cell layer was provided on the upper face of the filter and in which no cell layer was provided on the lower face of the filter (also referred to as the "VEC-TEM inserts"), and TEM inserts in which a smooth muscle cell layer was provided on the lower face of the filter and in which no cell layer was provided on the upper face of the filter (also referred to as the "SMC-TEM inserts"), were prepared.

[Permeability Assay]
(1) 2 mg of FITC-dextran 70 (70 kDa, Sigma) was dissolved in 8 ml of HBSS (+) (084-08965, Wako), to prepare a 250 µg/ml FITC-dextran 70 solution. The FITC-dextran 70 solution was stored in a light-shielded condition.
(2) 900 µl/well of HBSS (+) was added into each of the wells in the first to third columns of a 24-well plate
(3) Inserts having a cell layered body were taken out of the culture medium, and culture medium was removed from the inner side of each insert using an aspirator. The inserts were placed in wells in the first column.
(4) 200 µl of the FITC-dextran 70 solution was added to the inner side of each of the inserts put in the wells in the first column, and incubated at 37° C. for 10 minutes.
(5) The inserts were transferred to wells in the second column, and incubated at 37° C. for 10 minutes.
(6) The inserts were transferred to wells in the third column, and light-shielded by covering the plate with an aluminum sheet.
(7) Each of the sample liquids in the wells in the first and second columns was mixed using a pipette, and 100 µl of the sample liquid was sampled from each of the wells and transferred to a 96-well black plate. The 96-well black plate was light-shielded by being covered with an aluminum sheet.
(8) The fluorescent intensity of the FITC in each sample liquid was measured using a plate reader (ENSPIRE, PerkinElmer) with an excitation wavelength (Ex) of 485 nm, an emission wavelength (Em) of 530 nm and a number of flashes of 60 times.

Figure 9:
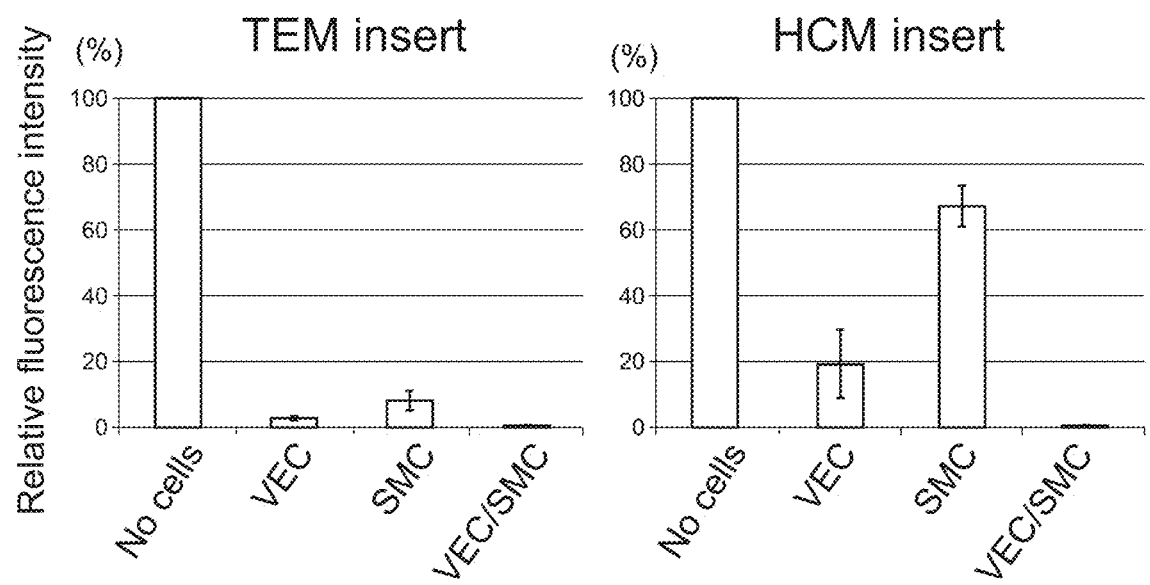
FIG. 9 is a graph showing a relative fluorescent intensity of FITC-dextran 70.

The relative fluorescent intensity of the FITC in the sample liquids (i.e., the relative amount of FITC-dextran 70 that leaked within 10 minutes from the addition of the FITC-dextran 70 solution) in the wells in the first column is shown in FIG. 9. The graph in FIG. 9 shows the relative fluorescent intensity in which the fluorescent intensity in the insert having no cell layer on either face of the filter is taken as the standard.

In the case of the TEM inserts, the VEC-TEM inserts exhibited a relative intensity of 3.0±0.5% (n=5), the SMC-TEM inserts exhibited a relative intensity of 8.2±2.9% (n=5), and the VEC/SMC-TEM inserts exhibited a relative intensity of 0.4±0.2% (n=5). The relative fluorescent intensity of the SMC-TEM inserts was the above-noted value although smooth muscle cell layers in general do not have highly tight cell-cell bonding. Therefore, this result presumably indicates that the TEM itself performs a barrier function against FITC-dextran 70 in the TEM inserts.

In the case of the HCM inserts, the VEC-HCM inserts exhibited a relative intensity of 19.3±10.2% (n=5), the SMC-HCM inserts exhibited a relative intensity of 67.4±6.1% (n=5), and the VEC/SMC-HCM inserts exhibited a relative intensity of 0.4±0.3% (n=5). The barrier function against FITC-dextran 70 was acquired by forming a vascular endothelial cell layer on one face of a HCM, and forming a smooth muscle cell layer on the other face of the HCM.

[Permeability Assay with Histamine]
 (1) 2 mg of FITC-dextran 70 (70 kDa, Sigma) was dissolved in 8 ml of HBSS (+) (084-08965, Wako), to prepare a 250 µg/ml FITC-dextran 70 solution. The FITC-dextran 70 solution was stored in a light-shielded condition. Histamine was dissolved in HBSS (+), to prepare a histamine solution.
 (2) 900 µl/well of HBSS (+) was added into each of the wells in the first to third columns of a 24-well plate.
 (3) Inserts having a cell layered body were taken out of the culture medium, and culture medium was removed from the inner side of each insert using an aspirator. The inserts were placed in wells in the first column.
 (4) The histamine solution was added to the wells at a final concentration of 10 µM or 100 µM, and incubated for 120 minutes.
 (5) 200 µl of the FITC-dextran 70 solution was added to the inner side of each of the inserts put in the wells in the first column, followed by incubation at 37° C. for 10 minutes.
 (6) The inserts were transferred to wells in the second column, and incubated at 37° C. for 10 minutes.
 (7) The inserts were transferred to wells in the third column, and light-shielded by covering the plate with an aluminum sheet.
 (8) Each of the sample liquids in the wells in the first and second columns was mixed using a pipette, and 100 µl of the sample liquid was sampled from each of the wells and transferred to a 96-well black plate. The 96-well black plate was light-shielded by being covered with an aluminum sheet.
 (9) The fluorescent intensity of the FITC in each sample liquid was measured using a plate reader (ENSPIRE, PerkinElmer) with an excitation wavelength (Ex) of 485 nm and an emission wavelength (Em) of 530 nm.

Figure 10:
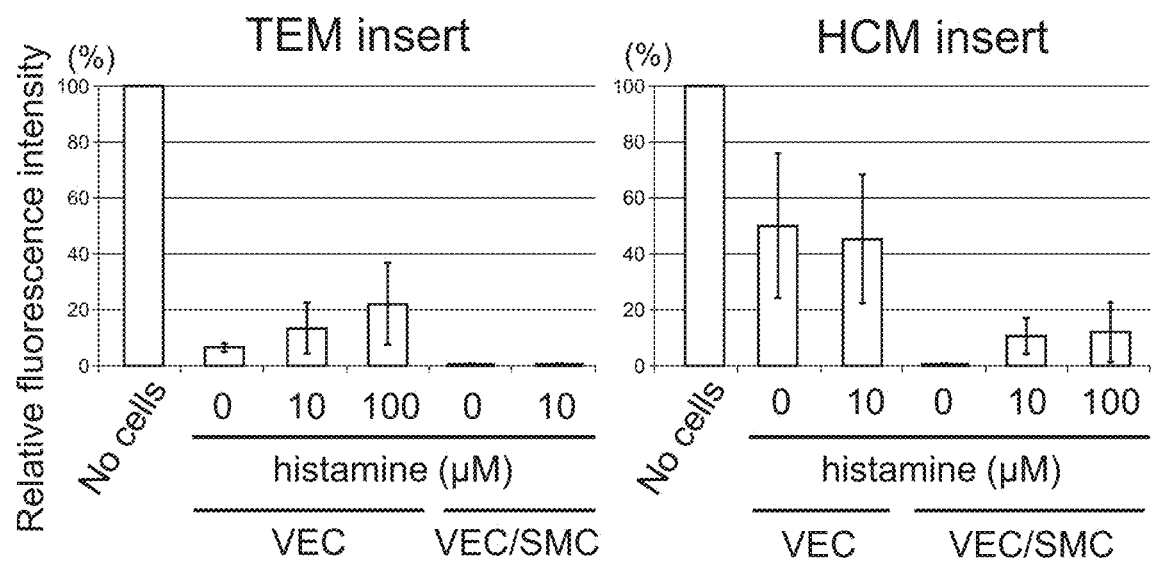
FIG. 10 is a graph showing a relative fluorescent intensity of FITC-dextran 70.

The relative fluorescent intensity of the FITC in the sample liquids (i.e., the relative amount of FITC-dextran 70 that leaked within 10 minutes from the addition of the FITC-dextran 70 solution) in the wells in the first column is shown in FIG. 10. The graph in FIG. 10 shows the relative fluorescent intensity in which the fluorescent intensity in the insert having no cell layer on either face of the filter is taken as the standard.

Histamine has an activity of enhancing substance permeability of vascular endothelial cells. The VEC/SMC-HCM insert exhibited an increase in FITC-dextran 70 permeability depending on the concentration of histamine. Further, the results demonstrated that the VEC/SMC-HCM insert has a function similar to vascular walls in living organisms. Moreover, the results demonstrated that the effect on vascular walls exerted by a test substance can be evaluated at high sensitivity by using the VEC/SMC-HCM insert.

Example 2

[Material]
 24-well plate: suspension culture quality (#662-102, Greiner).
 HCM insert: 24-well hanging insert in which a porous membrane with a honeycomb structure is provided at a filter portion, the porous membrane having a pore size of 3.0 µm, a thickness of 1.2 µm, and an aperture ratio of 55%, and the hanging insert being made of polycarbonate.
 coating material for HCM: collagen I from rat tail (#354236, Corning)
[Cells]
 vascular endothelial cell: rat vascular endothelial cells (#cAP-r0001, Angioproteomie)
 smooth muscle cell: rat smooth muscle cells (#R-ASM-580, Lonza)
[Liquid Culture Medium and Cell Detachment Reagent]
 Rat Endothelial Cell Growth Medium (#cAP-03, cAP-04, Angioproteomie) for rat vascular endothelical cells.
 DEMEM: F-12 (1:1) Culture Medium (#BE04-687Q, Lonza) for rat smooth muscle cells
 Accutase (AT104-500, Innovative cell technologies)
[Sterilization of HCM]
Sterilization of HCM was carried out in the same manner as that in Example 1.
[Collagen Coating of HCM]
 (1) Collagen I was dissolved in a 0.2N acetic acid solution, to prepare a 50 µg/ml collagen I solution.
 (2) 70 µl of the collagen I solution was spotted on central portions of wells of a 24 well-plate.
 (3) The HCM inserts were taken out of the PBS, and PBS was removed from the inner side of each HCM insert using an aspirator and the HCM inserts were immediately put on the collagen I solution spots on the wells, to immerse their HCMs in the collagen I solution.
 (4) 100 µl of the collagen I solution was added to the inner side of each HCM insert, and was left to stand still at room temperature for four hours (or left to stand still at 4° C. overnight).
 (5) 500 µl of PBS was added to neutralize the HCM.
[Cell Culture Using HCM Insert (Preparation of Cell Layered Body)]
 (1) 80 µl of a cell suspension liquid of rat smooth muscle cells was put, in a dome shape, on central portions of wells of a 24-well plate.
 (2) The coated HCM inserts were each placed on the cell suspension liquid of rat smooth muscle cells, thereby sandwiching the cell suspension liquid between the bottom face of the well and the HCM.
 (3) The plate and the HCM inserts were turned upside down in a state in which the cell suspension liquid was sandwiched between the bottom face of the well and the HCM. The plate and the HCM inserts in the turned state were placed in an incubator (37° C., 5% (v/v) $CO_2$) and cultured for 16 hours.
 (4) 1200 µl of the rat endothelial cell growth medium was added to the outer side of each HCM insert. The plate and the HCM inserts were taken out of the incubator, the orientation of the plate and the HCM inserts was returned to the initial orientation, and the HCM inserts were transferred to wells that contained a culture medium. Thereafter, 300 µl of a cell suspension liquid of rat vascular endothelial cells was inoculated in the inner side of each HCM insert.

(5) The plate and the HCM inserts were put in an incubator (37° C., 5% (v/v) $CO_2$), and cultured for 80 hours.

The inoculation conditions for the respective types of cells were as follows.

Rat smooth muscle cells: the culture area was 0.785 $cm^2$, the inoculation density was $1.0 \times 10^4$ cells/$cm^2$, and the volume of the cell suspension liquid was 80 µl.

Rat vascular endothelial cells: the culture area was 0.32 $cm^2$, the inoculation density was $5.0 \times 10^4$ cells/$cm^2$, and the volume of the cell suspension liquid was 300 µl.

As a result of the above cultivation, HCM inserts in which a vascular endothelial cell layer was provided on the upper face of the filter, and in which a smooth muscle cell layer was provided on the lower face of the filter (also referred to as the "VEC/SMC-HCM inserts") were obtained. The cell layer on the upper face immunofluorescence-stained for VE-cadherin, and the cell layer on the lower face immunofluorescence-stained for calponin, are shown in FIG. 11.

Figure 11:
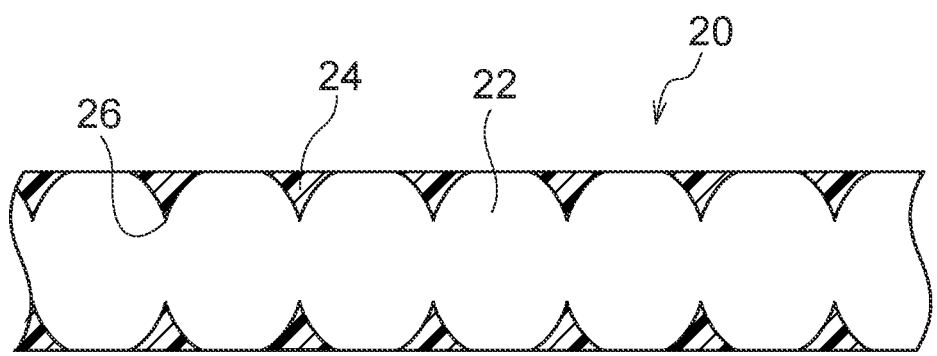
FIG. 11 is a schematic cross-sectional view illustrating one example of a porous membrane having communication holes.

As shown in FIG. 11, formation of a confluent cell layer and localization of vascular endothelial cadherin were clearly observed. The localization of vascular endothelial cadherin indicates strong adhesion between vascular endothelial cells (formation of cell-cell junctions), and is a feature characteristic to actual blood vessels. Thus, a cell layered body having a structure similar to a living tissue was prepared by forming a vascular endothelial cell layer on one side of the HCM and forming a smooth muscle cell layer on the other side of the HCM.

[Evaluation of Response to Physiologically Active Substance]

(1) 0.1 mg (100 units) of thrombin (#T7009-100UN, Sigma) was dissolved in 100 µl of physiological saline to prepare a thrombin solution at a concentration of 1000 U/mL. The thrombin solution was diluted with HBSS (+) to prepare a 25U/mL thrombin solution and a 100 U/mL thrombin solution.

(2) 900 µL of HBSS (+) was added into each of the wells of a 24-well plate.

(3) The inserts provided with the cell layered body were taken out of the culture medium, the culture medium was removed from the inner side of each insert using an aspirator, and the inserts were placed in the wells.

(4) HBSS (+) (control), the 25U/mL thrombin solution, or the 100 U/mL thrombin solution was added, in an amount of 200 µL, to the inner side of each of the inserts placed on the wells, and the inserts were incubated at 37° C. for 30 minutes.

(5) The cell layered body was observed under a microscope. The micrograph of the cell layered body is shown in FIG. 12, which is a superposed image of red fluorescence from VE-cadherin and green fluorescence from α-smooth muscle actin.

Figure 12:
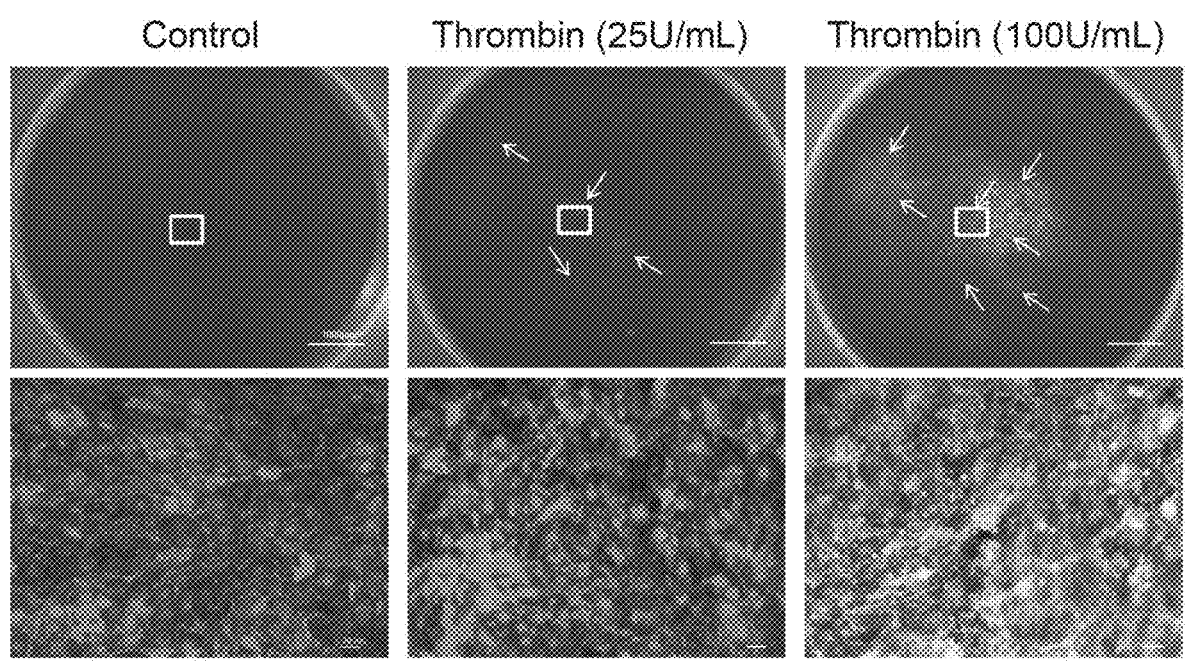
FIG. 12 is an immunofluorescent image of a cell layered body in Example 2.

As shown in FIG. 12, cell contraction due to activation of actin stress fibers caused by the addition of thrombin was observed. It was observed that the cell contraction occurred in the direction indicated by the arrow at the upper portion of FIG. 12. Higher thrombin concentrations caused stronger cell contractions. It was thus confirmed that the cell layered body having a vascular endothelical cell layer on one side of a HCM and a smooth muscle cell layer on the other side of the HCM reacts to a physiologically active substance in a manner similar to that exhibited by living tissues.

The disclosure of U.S. patent application Ser. No. 15/618,150, filed Jun. 9, 2017, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A living tissue model device comprising:
a first liquid compartment in which a first liquid composition is stored;
a second liquid compartment in which a second liquid composition is stored; and
a cell layered body disposed between the first liquid compartment and the second liquid compartment, as a partition between the first and second liquid compartments,
the cell layered body including a porous membrane having a honeycomb structure, a cell layer containing a first type of cells and disposed on one face of the porous membrane, and a cell layer containing a second type of cells different from the first type and disposed on another face of the porous membrane, the porous membrane having a plurality of apertures and an aperture ratio of from 30% to 70%,
wherein the plurality of apertures in the porous membrane are openings of a plurality of through-holes, and adjacent through-holes communicate with one another by communication holes in the interior of the porous membrane.

2. The living tissue model device according to claim 1, wherein the first type of cells and the second type of cells are two types of cells selected from the group consisting of parenchymal cells, stromal cells, myocytes, fibroblasts, nerve cells, glial cells, endothelial cells and epithelial cells.

3. The living tissue model device according to claim 1, wherein a material of the porous membrane comprises at least one selected from the group consisting of polybutadiene, polystyrene, polycarbonate, polysulfone, polyurethane, polylactic acid, a polylactic acid-polyglycolic acid copolymer, a polylactic acid-polycaprolactone copolymer, polyethylene terephthalate, poly(glycerol sebacate), polyacrylate, polymethacrylate, polyacrylamine, polyethylene naphthalate, polyethylene succinate, polybutylene succinate, polycaprolactone, polyamide, polyimide, a polysiloxane derivative and triacetylcellulose.

4. The living tissue model device according to claim 1, wherein each face of the porous membrane is covered by at least one selected from the group consisting of fibronectin, collagen, laminin, vitronectin, gelatin, perlecan, nidogen, proteoglycan, osteopontin, tenascin, nephronectin, a basement membrane matrix, a recombinant peptide and polylysine.

5. The living tissue model device according to claim 1, wherein an average diameter of the openings of the through-holes in the porous membrane is from 1 µm to 20 µm.

6. The living tissue model device according to claim 1, wherein the shape of the through-holes is a truncated sphere shape.

7. The living tissue model device according to claim 1, wherein the through-holes are arranged regularly.

8. The living tissue model device according to claim 1, wherein the honeycomb structure is a structure in which numerous through-holes are formed by partitioning by partition walls.

9. A method of evaluating a test substance, providing the living tissue model device of claim 1; the method comprising:
adding a test substance to at least one of the first liquid compartment or the second liquid compartment;
at least one process of (i) quantifying at least one of a chemical substance contained in the first liquid compartment or a cell contained in the first liquid compartment, or (ii) quantifying at least one of a chemical substance contained in the second liquid compartment or a cell contained in the second liquid compartment; and
based on a quantified amount obtained via at least one of process (i) or process (ii), determining whether or not the test substance causes an effect on a cellular tissue and a degree of the effect.

10. The method of evaluating a test substance according to claim 9, wherein process (i) comprises quantifying at least one of a miRNA contained in the first liquid compartment, a protein contained in the first liquid compartment or a transcription factor contained in the first liquid compartment, and process (ii) comprises quantifying at least one of a miRNA contained in the second liquid compartment, a protein contained in the second liquid compartment or a transcription factor contained in the second liquid compartment.

11. The method of evaluating a test substance according to claim 9, wherein the process (i) or (ii) further comprises adding a tracer to the liquid compartment to which the test substance has been added and measuring an amount of the tracer that has leaked from the liquid compartment to which the tracer has been added in process (i) or (ii) into the other liquid compartment.

12. A vascular wall model comprising:
a porous membrane having a honeycomb structure;
a vascular endothelial cell layer disposed on one face of the porous membrane; and
a smooth muscle cell layer, or a mesenchymal stem cell layer, disposed on another face of the porous membrane,
the porous membrane having a plurality of apertures and an aperture ratio of from 30% to 70%,
wherein the plurality of apertures in the porous membrane are openings of a plurality of through-holes, and adjacent through-holes communicate with one another by communication holes in the interior of the porous membrane.

13. The vascular wall model according to claim 12, wherein a FITC-dextran 70 permeability from a vascular endothelial cell layer side to a smooth muscle cell layer side or a mesenchymal stem cell layer side in the vascular wall model is from 0% to 10% of a FITC-dextran 70 permeability from one face of the porous membrane to the other face of the porous membrane.

14. The vascular wall model according to claim 12, wherein a material of the porous membrane comprises at least one selected from the group consisting of polybutadiene, polystyrene, polycarbonate, polysulfone, polyurethane, polylactic acid, a polylactic acid-polyglycolic acid copolymer, a polylactic acid-polycaprolactone copolymer, polyethylene terephthalate, poly(glycerol sebacate), polyacrylate, polymethacrylate, polyacrylamine, polyethylene naphthalate, polyethylene succinate, polybutylene succinate, polycaprolactone, polyamide, polyimide, a polysiloxane derivative and triacetylcellulose.

15. The vascular wall model according to claim 12, wherein each face of the porous membrane is covered by at least one selected from the group consisting of fibronectin, collagen, laminin, vitronectin, gelatin, perlecan, nidogen, proteoglycan, osteopontin, tenascin, nephronectin, a basement membrane matrix, a recombinant peptide and polylysine.

16. The vascular wall model according to claim 12, wherein an average diameter of the openings of the through-holes in the porous membrane is from 1 μm to 20 μm.

17. The living tissue model device according to claim 12, wherein the shape of the through-holes is a truncated sphere shape.

18. The living tissue model device according to claim 12, wherein the through-holes are arranged regularly.

19. The living tissue model device according to claim 12, wherein the honeycomb structure is a structure in which numerous through-holes are formed by partitioning by partition walls.

20. A vascular wall model device comprising a first liquid compartment in which a first liquid composition is stored; a second liquid compartment in which a second liquid composition is stored; and the vascular wall model of claim 12 disposed between the first liquid compartment and the second liquid compartment, as a partition between the first and second liquid compartments.

21. A method of evaluating a test substance, providing the vascular wall model device of claim 20; the method comprising:
adding a test substance to at least one of the first liquid compartment or the second liquid compartment;
at least one process of (i) quantifying at least one of a chemical substance contained in the first liquid compartment or a cell contained in the first liquid compartment, or (ii) quantifying at least one of a chemical substance contained in the second liquid compartment or a cell contained in the second liquid compartment; and
based on a quantified amount obtained via at least one of process (i) or process (ii), determining whether or not the test substance causes an effect on a cellular tissue and a degree of the effect.

22. The method of evaluating a test substance according to claim 21, wherein process (i) comprises quantifying at least one of a miRNA contained in the first liquid compartment, a protein contained in the first liquid compartment or a transcription factor contained in the first liquid compartment, and process (ii) comprises quantifying at least one of a miRNA contained in the second liquid compartment, a protein contained in the second liquid compartment or a transcription factor contained in the second liquid compartment.

23. The method of evaluating a test substance according to claim 21, wherein one of the first liquid compartment or the second liquid compartment is a liquid compartment in which blood, a liquid composition containing erythrocytes or a liquid composition mimicking blood and containing at least one selected from the group consisting of dextran, Evans Blue, fluorescein sodium salt and FITC-microbeads is stored, the adding of a test substance to at least one of the first liquid compartment or the second liquid compartment comprises adding the test substance to the liquid compartment in which blood, a liquid composition containing erythrocytes or a liquid composition mimicking blood and containing at least one selected from the group consisting of dextran, Evans Blue, fluorescein sodium salt and FITC-microbeads is stored, and determining, based on the at least one process, at least one of an amount of erythrocytes that have leaked from the liquid compartment to which the test substance has been added to the other liquid compartment, an amount of hemoglobin that has leaked from the liquid compartment to which the test substance has been added to the other liquid compartment or an amount of at least one selected from the group consisting of dextran, Evans Blue, fluorescein sodium salt and FITC-microbeads that has leaked from the liquid compartment to which the test substance has been added to the other liquid compartment.

* * * * *